United States Patent [19]
Farr et al.

[11] Patent Number: 5,811,231
[45] Date of Patent: Sep. 22, 1998

[54] METHODS AND KITS FOR EUKARYOTIC GENE PROFILING

[75] Inventors: Spencer B. Farr, Longmont; Marque D. Todd, Westminster, both of Colo.

[73] Assignees: Pres. and Fellows of Harvard College, Cambridge, Mass.; Xenometrix, Inc.

[21] Appl. No.: 374,641

[22] PCT Filed: Jan. 21, 1994

[86] PCT No.: PCT/US94/00583

§ 371 Date: Jul. 21, 1995

§ 102(e) Date: Jul. 21, 1995

[87] PCT Pub. No.: WO94/17208

PCT Pub. Date: Aug. 4, 1994

Related U.S. Application Data

[63] Continuation of Ser. No. 8,896, Jan. 21, 1993, abandoned.

[51] Int. Cl.⁶ ............. C12Q 7/68; C07H 21/02; C07H 21/04; A01N 59/00

[52] U.S. Cl. ............. 435/6; 435/29; 435/32; 435/870; 435/91.2; 536/23.1; 536/24.3; 536/24.33; 536/24.1; 424/600; 424/94.1; 424/278.1; 424/178.1

[58] Field of Search ............. 435/6, 29, 32, 435/870; 536/23.1, 29.1, 24.3, 24.33; 424/500, 94.1, 278.1, 178.1

[56] References Cited

U.S. PATENT DOCUMENTS

| | | | |
|---|---|---|---|
| 4,849,335 | 7/1989 | Hofnung et al. | 435/6 |
| 4,997,757 | 3/1991 | Schiestl | 435/172.1 |
| 5,149,634 | 9/1992 | Bradley | 435/29 |
| 5,232,833 | 8/1993 | Sanders et al. | 435/7.21 |
| 5,401,629 | 3/1995 | Harpold et al. | |
| 5,436,128 | 7/1995 | Harpold et al. | |
| 5,612,318 | 3/1997 | Weichselbaum et al. | 514/44 |
| 5,665,543 | 9/1997 | Foulkes et al. | |

FOREIGN PATENT DOCUMENTS

| | | | |
|---|---|---|---|
| 0 325 849 | 8/1989 | European Pat. Off. | C12N 15/00 |
| 0 353 812 | 2/1990 | European Pat. Off. | C12Q 1/68 |
| 0 516 443 | 12/1992 | European Pat. Off. | C12Q 1/66 |
| WO 90/10710 | 9/1990 | WIPO | C12Q 1/00 |
| WO 91/01379 | 2/1991 | WIPO . | |
| WO 92/05286 | 4/1992 | WIPO | C12Q 1/68 |
| WO 92/17605 | 10/1992 | WIPO | C12Q 1/02 |

OTHER PUBLICATIONS

H.D. Bradshaw, Jr. et al., "Human Thymidine Kinase Gene: Molecular Cloning and Nucleotide Sequence of a cDNA Expressible in Mammalian Cells", *Mol. Cell. Biol.* vol. 4 pp. 2316–2320 (1984).

P. D'Arpa et al., "cDNA cloning of human DNA topoisomerase I: Catalytic activity of a 67.7–kDa carboxyl–terminal fragment", *Proc. Natl. Acad. Sci. USA*, 85, pp. 2543–2547 (1988).

(List continued on next page.)

*Primary Examiner*—W. Gary Jones
*Assistant Examiner*—Dianne Rees
*Attorney, Agent, or Firm*—Fish & Neave; James F. Haley, Jr., Esq.; Andrew S. Marks, Esq.

[57] ABSTRACT

This invention provides methods and diagnostic kits for identifying and characterizing toxic compounds. These methods and diagnostic kits measure transcription or translation levels from genes linked to native eukaryotic stress promoters, especially those of mammals. The kits and methods of this invention utilize at least one stress promoter from each of the following groups: redox stress, DNA stress, protein stress and energy/ionic stress. The invention also provides methods and diagnostic kits for identifying and characterizing compounds that are toxic to specific organs, such as skin and the eye, as well as for each of the individual stresses indicated above. The methods and diagnostic kits of this invention yield information concerning the action of a compound on a subcellular level. This information may be utilized to design antitoxins to compounds found to be toxic and in active drug design.

40 Claims, 11 Drawing Sheets

OTHER PUBLICATIONS

E. Danciger et al., "Human Cu/Zn superoxide dismutase gene family: Molecular structure and characterization of four Cu/Zn superoxide dismutase–related pseudogenes", *Proc. Natl. Acad. Sci. USA,* 83, pp. 3619–3623 (1986).

M. S. Denison, The DNA Recognition Site for the Dioxin–Ah Receptor Complex, *J. Biol. Chem.,* vol. 263, pp. 17221–17224.

R. A. Dixon, "The Phytoalexin Response: Elicitation, Signalling And Control Of Host Gene Expression", *Biol. Rev.,* v. 61, pp. 239–291 (1986).

T. H. Murphy et al., "Enhanced NAD(P)H:Quinone Reductase Activity Prevents Glutamate Toxicity Produced by Oxidative Stress", *J. Neurochem.,* vol. 56, pp. 990–995 (1991).

T. Nguyen et al., "Regulation of Rat Glutathione S–Transferase Ya Subunit Gene Expression", *J. Biol. Chem.,* vol. 267, pp. 13535–13539 (1992).

L. M. Nutter et al., "DNA Strand Scission and Free Radical Production in Menadione–treated Cells",*J. Biol. Chem.,* vol. 267, pp. 2474–2479 (1992).

W. J. Roseler et al. "Cyclic AMP and the Induction of Eukaryotic Gene Transcription", *J. Biol. Chem.,* vol. 263, pp. 9063–9066 (1988).

R. Schreck et al., "Reactive oxygen intermediates as apparently widely used messengers in the activation of the NF–kB transcription factor and HIV–1", *EMBO J,* vol. 10, pp. 2247–2258 (1991).

J. A. Silverman et al., "Cloning and characterization of a member of the rat multidrug resistance (mdr) gene family", *Gene,* vol. 106, pp. 229–236 (1991).

R. C. Skoda et al., "Human Microsomal Xenobiotic Epoxide Hydrolase",*J. Biol. Chem.,* vol. 263, pp. 1549–1554 (1988).

E. Stringham et al., "Temporal and Spatial Expression Patterns of the Small Heat Shock (hsp16) Genes in Transgenic Caenorhabditis elegans", *Mol. Biol. Cell,* vol. 3, pp. 221–233 (1992).

K. Tano et al., "Isolation and structural characterization of a cDNA clone encoding the human DNA repair protein for $O^6$–alkylguanine", *Proc. Natl. Acad. Sci. USA* vol. 87, pp. 686–690, (1990).

M. Tsai–Pflugfelder et al., "Cloning and sequencing of cDNA encoding human DNA topoisomerase II and localization of the gene to chromosome region 17q21–22", *Proc. Natl. Acad. Sci. USA,* vol. 85, pp. 7177–7181 (1988).

K. Uchida et al., "Nucleotide Sequence Of A Full–Length cDNA For Human Fibroblast Poly(ADP–Ribose) Polymerase", *Biochem. Biophys. Res. Comm.,* vol. 148, pp. 617–622 (1987).

F. van Straaten et al., "Complete nucleotide sequence of a human c–one gene: Deduced amino acid sequence of the human c–fos protein", *Proc. Natl. Acad. Sci. USA,* vol. 80, pp. 3183–3187 (1983).

M. Wathelet et al., "Full–length sequence and expression of the 42 kDA 2–5A synthetase induced by human interferon", *FEBS Lett.,* vol. 196, pp. 113–120.

J. E. Freeman et al., "cDNA Sequence, Deduced Amino Acid Sequence, Predicted Gene Structure and Chemical Regulation of Mouse Cyp2e1", *Biochem. J.* vol. 281, pp. 689–695 (1992).

Y. Fujii–Kuriyama et al., "Regulation of CYP1A1 expression", *FASEB J.,* vol. 6, pp. 706–710 (1992).

B. Grima et al., "A single human gene encoding multiple tyrosine hydroxylases with different predicted functional characteristics", *Nature,* vol. 326, pp. 707–711 (1987).

P. Herrlich et al., "The Mammalian Genetic Stress Response", *Adv. Enzyme Regul.,* vol. 25, pp. 485–504 (1986).

N. Hickok e al., "Complete Amino Acid Sequence of Human Ornithine Decarboxylase Deduced from Complementary DNA", *DNA,* vol. 6, pp. 179–187 (1987).

L. C. Hsu et al., "Cloning of cDNAs for human aldehyde dehydrogenases 1 and 2", *Proc. Natl. Acad. Sci., USA,* vol. 82, pp. 3771–3775 (1985).

C. Hunt et al., "Conserved features of eukaryotic hsp70 genes revealed by comparison with the nucleotide sequence of human hsp70", *Proc. Natl. Acad. Sci. USA,* vol. 82, pp. 6455–6459 (1985).

T. Iyanagi et al., "Cloning and Characterization of cDNA Encoding 3–Methylcholanthrene Inducible Rat mRNA for UDP–glucuronosyltransferase",*J. Biol. Chem.,* vol. 261, pp. 15607–15614 (1986).

D. Jaskulski, "Regulation of the Proliferating Cell Nuclear Antigen Cyclin and thymidine Kinase mRNA Levels by Growth Factors",*J. Biol. Chem.,* vol. 263, pp. 10175–10179 (1988).

M. Karin et al., "Human metallothionein genes–primary structure of the metallothionein–II gene and a related processed gene", *Nature,* vol. 299, pp. 797–802 (1982).

A. J. Korman et al., "The amino acid sequence and gene organization of the heavy chain of the HLA–DR antigen: Homology to immunoglobulins", *Proc. Natl. Acad. Sci. USA,* vol. 79, pp. 6013–6017 (1982).

J. McCann et al., "Detection of Carcinogens as Mutagens in the Salmonella/Microsome test: Assay of 300 Chemicals", *Proc. Natl. Acad. Sci. USA,* vol. 72, pp. 5135–5139 (1975).

J. S. Miles et al., "A novel human cytochrome P450 gene (P450IIB): chromosomal localization and evidence of alternative splicing", *Nucl. Acids Res.,* vol. 16, pp. 5783–5795 (1988).

S. Miyazawa et al., Complete Nucleotide Sequence of cDNA and Predicted Amino Acid Sequence of Rat Acyl–CoA Oxidase, *J. Biol. Chem.,* vol. 262, pp. 8131–8137 (1987).

D. D. Mosser, "Coordinate Changes in Heat Shock Element–Binding Activity and HSP70 Gene Transcription Rates in Human Cells", *Mol. Cell. Biol.,* vol. 8, pp. 4736–4744 (1988).

Methapyrilene hydrochloride

Sodium Arsenate

All Trans Retinoic Acid

SEQUENCE LISTING ( 1 ) GENERAL INFORMATION:

( i i i ) NUMBER OF SEQUENCES: 45

( 2 ) INFORMATION FOR SEQ ID NO:1:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
AAAAAACCC  AGTCCAACTA  CAGACATGGC  AGCTGAGTCC  CTGCCATTCA  CCTTGGAGAC         60
GGTGTTTTTT                                                                   70
```

( 2 ) INFORMATION FOR SEQ ID NO:2:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

```
AAAAAAGGCC  AGTATGCACA  GCTTTCCTCC  ACTGCTGCTG  CTGCTGTTCT  GGGGTGTGGT         60
GTCTTTTTT                                                                    69
```

( 2 ) INFORMATION FOR SEQ ID NO:3:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

```
AAAAAACCCC  AAGATCCTGA  AACAGAGCAT  GACCCTGAAC  CTGGCCGACC  CAGTTTTTT          59
```

( 2 ) INFORMATION FOR SEQ ID NO:4:

(i) SEQUENCE CHARACTERISTICS:
  (A) LENGTH: 63 base pairs
  (B) TYPE: nucleic acid
  (C) STRANDEDNESS: single
  (D) TOPOLOGY: linear (xi) SEQUENCE DESCRIPTION: SEQ ID NO:4:

```
AAAAACAAC CTGAACGTCA ACGAGGAGAA GTACCAGGAG GCGTTGGCCA AGGGAGATTT    60
TTT                                                                63
```

(2) INFORMATION FOR SEQ ID NO:5:

(i) SEQUENCE CHARACTERISTICS:
    (A) LENGTH: 60 base pairs
    (B) TYPE: nucleic acid
    (C) STRANDEDNESS: single
    (D) TOPOLOGY: linear (xi) SEQUENCE DESCRIPTION: SEQ ID NO:5:

```
AAAAATAGA GCGTCCGCAA CCCGACAGCA TGCCCCAGGA TTTGTCAGAG GCCCTTTTT    60
```

(2) INFORMATION FOR SEQ ID NO:6:

(i) SEQUENCE CHARACTERISTICS:
    (A) LENGTH: 65 base pairs
    (B) TYPE: nucleic acid
    (C) STRANDEDNESS: single
    (D) TOPOLOGY: linear (xi) SEQUENCE DESCRIPTION: SEQ ID NO:6:

```
AAAAAGGAG TTGGGAGCTG AGTGGAGAAG AAGCCACGAC TCTCGCTAGG TCAGTACTCT    60
TTTTT                                                              65
```

(2) INFORMATION FOR SEQ ID NO:7:

(i) SEQUENCE CHARACTERISTICS:
    (A) LENGTH: 69 base pairs
    (B) TYPE: nucleic acid
    (C) STRANDEDNESS: single
    (D) TOPOLOGY: linear (xi) SEQUENCE DESCRIPTION: SEQ ID NO:7:

```
AAAAAGCCG CGGCAGTCGG CATCGACCTG GGCACCACCT ACTCCTGCGT GGGGGTGTTC    60
CAATTTTTT                                                          69
```

(2) INFORMATION FOR SEQ ID NO:8:

(i) SEQUENCE CHARACTERISTICS:
    (A) LENGTH: 62 base pairs
    (B) TYPE: nucleic acid
    (C) STRANDEDNESS: single
    (D) TOPOLOGY: linear (xi) SEQUENCE DESCRIPTION: SEQ ID NO:8:

```
AAAAAATTA CAGCAAGCCT GGAACCTATA GCCCCTTTAA CTTGAGCAGC ATCATTTTT    60
TT                                                                62
```

(2) INFORMATION FOR SEQ ID NO:9:

(i) SEQUENCE CHARACTERISTICS:
    (A) LENGTH: 62 base pairs
    (B) TYPE: nucleic acid
    (C) STRANDEDNESS: single
    (D) TOPOLOGY: linear (xi) SEQUENCE DESCRIPTION: SEQ ID NO:9:

```
AAAAAACATT CAGGGAAGGG TTGGGTAGGT AGCGAAGAAT AGGGATGAAG TCAGCTTTTT       60

TT                                                                     62
```

( 2 ) INFORMATION FOR SEQ ID NO:10:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

```
AAAAAAATGC TGGAGAAGGA GTCTGCGGGT GAGTGGTAGT AAGAGAGGCT ATCCCTTTT        60

TT                                                                     62
```

( 2 ) INFORMATION FOR SEQ ID NO:11:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

```
AAAAAGGAA TCTCATTTTC TAGCTTTGAT CTGGTTGTCA GTTGGGATGG ACTTGCTTTT        60

TT                                                                     62
```

( 2 ) INFORMATION FOR SEQ ID NO:12:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

```
AAAAACCTC TTGCTTCCCC GTGTTGATGT AGCCGAGGAT CTTCTTAAAC TGAGTTTTT         60

TT                                                                     62
```

( 2 ) INFORMATION FOR SEQ ID NO:13:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

```
AAAAACAGT GGTCAATGTC ACGTGGCTTC GAAATGGAAA ACCTGTCACC ACAGGATTT         60

TT                                                                     62
```

( 2 ) INFORMATION FOR SEQ ID NO:14:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

```
AAAAAGGAT TGTGAAATGA AACGCACCAC ACTGGACAGC CCGTTGGGGA AGCTGGAGCT        60

GTCTTTTTT                                                              69
```

( 2 ) INFORMATION FOR SEQ ID NO:15:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

```
AAAAAATTCT  TACAATTTTG  GTACCAGTGC  TTGACTAGGC  GGATGAGGCT  CTTGAGTTTT        60
TT                                                                            62
```

( 2 ) INFORMATION FOR SEQ ID NO:16:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

```
AAAAAAAGTC  TTGCATGATC  CTTGTCACAA  ATAGTTTAAG  ATGGCTGGG   TGATTCTTTT        60
TT                                                                            62
```

( 2 ) INFORMATION FOR SEQ ID NO:17:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

```
AAAAAACCAG  CACCCCGTCT  CCGCGACTAC  TTTATAGGCC  AGACCTTTTT  T                 51
```

( 2 ) INFORMATION FOR SEQ ID NO:18:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

```
AAAAAAAACC  GTACTCTCCC  AGTTCTCTTC  CATTTCCAGA  CATCTTGAAT  CCACCATTTT        60
TT                                                                            62
```

( 2 ) INFORMATION FOR SEQ ID NO:19:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

```
AAAAAAGAGT  GTCTTTGGCA  TACTTGATCA  CCAGGCACTT  GTACTGAGCA  ATCTGGTTTT        60
TT                                                                            62
```

( 2 ) INFORMATION FOR SEQ ID NO:20:

( i ) SEQUENCE CHARACTERISTICS:
        ( A ) LENGTH: 62 base pairs
        ( B ) TYPE: nucleic acid
        ( C ) STRANDEDNESS: single (D) TOPOLOGY: linear (xi) SEQUENCE DESCRIPTION: SEQ ID NO:20:

AAAAAAAAAC ACCTTCTTCA CATCATCCGC ACTCTTTTTC TTCAGGCCGA CCATTTTTTT 60

TT 62

(2) INFORMATION FOR SEQ ID NO:21:

(i) SEQUENCE CHARACTERISTICS:
      (A) LENGTH: 62 base pairs
      (B) TYPE: nucleic acid
      (C) STRANDEDNESS: single
      (D) TOPOLOGY: linear (xi) SEQUENCE DESCRIPTION: SEQ ID NO:21:

AAAAAGAAG CTCTCAGACA CGAAGTAGAC TGACTGGTAC GTCTGGTCTT GGTAGGTTTT 60

TT 62

(2) INFORMATION FOR SEQ ID NO:22:

(i) SEQUENCE CHARACTERISTICS:
      (A) LENGTH: 62 base pairs
      (B) TYPE: nucleic acid
      (C) STRANDEDNESS: single
      (D) TOPOLOGY: linear (xi) SEQUENCE DESCRIPTION: SEQ ID NO:22:

AAAAAATCTA GAATATAGGC AGCCAGACCC ACAGGAGAGT CATTCAGAGC AGAGCCTTTT 60

TT 62

(2) INFORMATION FOR SEQ ID NO:23:

(i) SEQUENCE CHARACTERISTICS:
      (A) LENGTH: 62 base pairs
      (B) TYPE: nucleic acid
      (C) STRANDEDNESS: single
      (D) TOPOLOGY: linear (xi) SEQUENCE DESCRIPTION: SEQ ID NO:23:

AAAAAGATA GCGCTCTTCT TCCCACCATT TCCACTTCTG TTCCTCTTCT TTCTTCTTTT 60

TT 62

(2) INFORMATION FOR SEQ ID NO:24:

(i) SEQUENCE CHARACTERISTICS:
      (A) LENGTH: 62 base pairs
      (B) TYPE: nucleic acid
      (C) STRANDEDNESS: single
      (D) TOPOLOGY: linear (xi) SEQUENCE DESCRIPTION: SEQ ID NO:24:

AAAAAGCCT CTGCCAGTTT TTCTTCAGTC ATCTTCACAA CAAATTTCAC AGTGGTTTTT 60

TT 62

(2) INFORMATION FOR SEQ ID NO:25:

(i) SEQUENCE CHARACTERISTICS:
      (A) LENGTH: 67 base pairs
      (B) TYPE: nucleic acid
      (C) STRANDEDNESS: single
      (D) TOPOLOGY: linear (xi) SEQUENCE DESCRIPTION: SEQ ID NO:25:

AAAAAATCTC TTCCTTGCAG GTGGCTCCTG CACCTGCACT GGCTCCTGCA AATGCAAAGA 60

GTTTTTT 67

(2) INFORMATION FOR SEQ ID NO:26:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:26:

AATTGCTATG GCGTGGTAAG TGCCCAGTGC CCCTTTGGTG GATTCAAGAT 50

(2) INFORMATION FOR SEQ ID NO:27:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:27:

ATCTGAGTTC CTACCTGAAC GGTTTCTCAC CCCTGATGGT GCTATCGACA 50

(2) INFORMATION FOR SEQ ID NO:28:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:28:

GTACTCCCAG CTGCACTGCT TACACGTCTT CCTTCGTCTT CACCT 45

(2) INFORMATION FOR SEQ ID NO:29:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:29:

AGGAGAATGA AAGGAAAGTG GCACAGCTAG CTGAAGAGAA TGAACGGCTC 50

(2) INFORMATION FOR SEQ ID NO:30:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (  i i  ) MOLECULE TYPE: cDNA (  i i i  ) HYPOTHETICAL: NO (  x i  ) SEQUENCE DESCRIPTION: SEQ ID NO:30:

AGTCGCTACA TGGATCAATG GGTTCCAGTG ATTAATCTCC CTGAACGGTG    50

( 2 ) INFORMATION FOR SEQ ID NO:31:

(  i  ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear (  i i  ) MOLECULE TYPE: cDNA (  i i i  ) HYPOTHETICAL: NO (  x i  ) SEQUENCE DESCRIPTION: SEQ ID NO:31:

GTGGTGGACC TGACCTGCCG TCTAGAAAAA CCTGCCAAAT ATGATGACAT    50

( 2 ) INFORMATION FOR SEQ ID NO:32:

(  i  ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear (  i i  ) MOLECULE TYPE: cDNA (  i i i  ) HYPOTHETICAL: NO (  x i  ) SEQUENCE DESCRIPTION: SEQ ID NO:32:

CAGCCCAAGG AAGCCTCCCA TGGATGAGAA ATCTTTAGAA GAAGCAAGGA    50

( 2 ) INFORMATION FOR SEQ ID NO:33:

(  i  ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear (  i i  ) MOLECULE TYPE: cDNA (  i i i  ) HYPOTHETICAL: NO (  x i  ) SEQUENCE DESCRIPTION: SEQ ID NO:33:

CTTACACTCA GCTTTCTGGT GGCGACAGTT GCTGTAGGGC TTTA    44

( 2 ) INFORMATION FOR SEQ ID NO:34:

(  i  ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear (  i i  ) MOLECULE TYPE: cDNA (  i i i  ) HYPOTHETICAL: NO (  x i  ) SEQUENCE DESCRIPTION: SEQ ID NO:34:

AGAAGGACGA GTTTGAGCAC AAGAGGAAGG AGCTGGAGCA GGTGT    45

( 2 ) INFORMATION FOR SEQ ID NO:35:

(  i  ) SEQUENCE CHARACTERISTICS:

(A) LENGTH: 50 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:35:

GCTCAGGGAA CAGGTGGCAC AGCTTAAACA GAAAGTCATG AACCACGTTA    50

(2) INFORMATION FOR SEQ ID NO:36:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:36:

GAAAGGCATC TATTTTTCAA TGGTCAGTGT CCAGGCTGGA ACAAAGCGCC    50

(2) INFORMATION FOR SEQ ID NO:37:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:37:

GCACTGGCTC CTGCAAATGC AAAGAGTGCA AATGCAACTC CTGCAAG    47

(2) INFORMATION FOR SEQ ID NO:38:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:38:

CCCAGGGCTG CATCTGCAAA GGGGCGTCGG ACAAG    35

(2) INFORMATION FOR SEQ ID NO:39:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:39:

ACCACTGTAT TTTGCTCCAA GCAGCCTCTT TGACCTAAAC TTCCAGGCAG    50

( 2 ) INFORMATION FOR SEQ ID NO:40:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( x i ) SEQUENCE DESCRIPTION: SEQ ID NO:40:

ACAAAAGCCA CTCCACTCTC TTCAACGGTG ACACTCAGTA TGTCTGCAGA　　　　　50

( 2 ) INFORMATION FOR SEQ ID NO:41:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( x i ) SEQUENCE DESCRIPTION: SEQ ID NO:41:

TTGCTCTCGA CAGTATCCAC AATAGCTGAC GGCTGGGTGT TTCAGTTTGA　　　　　50

( 2 ) INFORMATION FOR SEQ ID NO:42:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( x i ) SEQUENCE DESCRIPTION: SEQ ID NO:42:

ACCTTCCAGC AGATGTGGAT TAGCAAGCAG GAGTACGACG AGTCG　　　　　45

( 2 ) INFORMATION FOR SEQ ID NO:43:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( x i ) SEQUENCE DESCRIPTION: SEQ ID NO:43:

TTGAGTGGAT CCCCAACAAT GTGAAAACGG CTGTCTGTGA CATCCCACCT　　　　　50

( 2 ) INFORMATION FOR SEQ ID NO:44:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA (iii) HYPOTHETICAL: NO (xi) SEQUENCE DESCRIPTION: SEQ ID NO:44:

TACCAGGCAG CTTAACAAAG 20

(2) INFORMATION FOR SEQ ID NO:45:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (iii) HYPOTHETICAL: NO (xi) SEQUENCE DESCRIPTION: SEQ ID NO:45:

ACTGGCCTTT GTCTTCTTTC 20

METHODS AND KITS FOR EUKARYOTIC GENE PROFILING

This application is a 371 application of PCT/US94/00583 filed Jan. 21, 1994 which is a continuation of Ser. No. 08/008,896 filed Jan. 21, 1993, now abandoned.

TECHNICAL FIELD OF INVENTION

This invention provides methods and diagnostic kits for identifying and characterizing toxic compounds. These methods and diagnostic kits measure transcription or translation levels from genes linked to native eukaryotic stress promoters, especially those of mammals. The kits and methods of this invention utilize at least one stress promoter from each of the following groups: redox stress, DNA stress, protein stress and energy/ionic stress. The invention also provides methods and diagnostic kits for identifying and characterizing compounds that are toxic to specific organs, such as skin and the eye, as well as for each of the individual stresses indicated above. The methods and diagnostic kits of this invention yield information concerning the action of a compound on a subcellular level. This information may be utilized to design antitoxins to compounds found to be toxic and in active drug design.

BACKGROUND OF THE INVENTION

At least 55,000 chemicals are presently produced in the United States. Over 2,000 new chemicals are introduced into the market each year. Very few of these chemicals have been comprehensively tested for acute or chronic toxicity. For example, less than 1 percent of commercial chemicals have undergone complete health hazard assessment.

The Environmental Protection Agency ("EPA") has the authority to require toxicological testing of a chemical prior to commercial production, but that authority is rarely invoked. Less than 10 percent of new chemicals are subjected to detailed review by the EPA. In the interest of cost and speedy access to the market, the EPA often uses the toxicity of previously tested homologous compounds to gauge the toxicity of a new chemical.

The potential toxicity of new drugs is monitored by the Food and Drug Administration ("FDA"). For a New Drug Application (NDA), the FDA typically requires a large battery of toxicity, carcinogenicity, mutagenicity and reproduction/fertility tests in at least two species of live animals. These tests are required to last up to one year. A two year toxicity test in rats costs approximately $800,000 [*Casarett and Doull's Toxicology*, 4th Edition, M. O. Amdur et al., eds. Pergamon Press, New York, New York, p. 37 (1991)].

Besides cost, animal testing also presents disadvantages in terms of time, animal suffering and accuracy. Typical toxicity tests are divided into three stages: acute, short term and long term. Acute tests, which determine the $LD_{50}$ of a compound (the dose at which 50% of test animals are killed), require some 60–100 animals and a battery of tests for determining $LD_{50}$, dose-response curves and for monitoring clinical end points, other than death. Short term tests usually involve at least 24 dogs and 90 rats and last from 90 days in rats to 6–24 months in dogs. Body weight, food consumption, blood, urine and tissue samples are frequently measured in the short-term tests. In addition, dead animals are subjected to post-mortem examinations. Long term tests are similar to short term tests, but last 2 years in rats and up to 7 years in dogs or monkeys.

Animal testing has come under criticism by animal rights activists and the general public because of the severe suffering inflicted on the animals. Moreover, recent evidence calls into question the accuracy of animal testing. For example, variables, much as animal diet, may impair the predictability of animal tests in determining carcinogenic properties [P. H. Abelson, "Diet and Cancer in Humans and Rodents", *Science*, 255, p. 141 (1992)]. And prior determinations on dioxin toxicity, based on guinea pig testing, are now being reevaluated [B. J. Culliton, "U.S. Government Orders New Look At Dioxin", *Nature*, 352, p. 753 (1991); L. Roberts, "More Pieces in the Dioxin Puzzle", *Research News*, October 1991, p. 377]. It is therefore apparent that there is an urgent need for a quick, inexpensive and reliable alternative to toxicity testing in animals.

Several short-term alternative tests are available. For example, the Ames Assay detects carcinogens which cause genetic reversion of mutant strains of *Salmonella typhimurium*. However, the Ames Assay cannot detect either non-mutagenic carcinogens or non-carcinogenic toxins. The yeast carcinogen assay system described in U.S. Pat. No. 4,997,757 overcomes some of the drawbacks of the Ames Assay, but is still not able to detect non-carcinogenic toxins. Both of these assays are designed to detect alterations and mutations at the DNA level only. Therefore, those prior art tests cannot detect direct damage to proteins or lipid membranes, nor inhibitors of DNA synthesis. Moreover, those prior art tests cannot provide information as to how a mutagen or toxin exerts its effect.

WO 90/10710 describes the use of a TNF, IL-1α or IL-1β fused to a reporter gene to detect bacterial pyrogens. However, the disclosed assay is limited in that it detects only a particular stress (bacterial pyrogens) and yields no qualitative information about how the pyrogen exerts its toxic effect.

Applicant's copending U.S. application Ser. No. 07/910,793, filed Jul. 6, 1992, now abandoned the disclosure of which is herein incorporated by reference, describes an assay system which utilizes a reporter gene fused to bacterial stress promoters to determine and characterize the toxicity of a compound. This assay is able to detect damage to proteins or lipid membranes and inhibition of DNA synthesis. Thus, this assay provides for the identification of non-carcinogenic toxins. Unfortunately, the correlation between bacterial toxicity and toxicity to mammals and other higher eukaryotes has certain limitations and may not be an accurate measure of toxicity in higher animals.

Therefore, there is still a need for an assay that has the time and cost-saving features of the bacterial stress assay, but is based on a eukaryotic cell.

SUMMARY OF THE INVENTION

Applicant has fulfilled this need by providing an in vitro diagnostic kit and assay method which identify and characterize the cellular and subcellular effect of a potential toxin on an animal cell. These kits and methods employ the native stress promoters of eukaryotic cells, preferably mammalian cells, and measure the level of transcription or translation of a gene which is operatively linked thereto. Depending upon the choice of stress promoters used, the kits and methods of this invention may be designed to identify and characterize compounds that are toxic to the whole animal or to specific organs of that animal.

In one embodiment, the kits and methods of this invention characterize the toxicity of a compound by determining the level of transcription of various stress genes present in a eukaryotic cell. These kits and methods employ oligonucleotides that are complementary or homologous to at least a portion of various stress gene messenger RNAs to detect transcription of those genes in the cell. In this embodiment a single cell is effectively an in vivo diagnostic reagent for determining what particular stress a given compound induces.

In another embodiment, each of a plurality of similar eukaryotic cells harbors a different stress promoter operatively linked to a reporter gene. By exposing each cell separately to a compound and measuring the expression of the reporter gene product, the toxicity of that compound may be characterized.

The kits and methods of this invention are optimally designed to determine the toxicity of a compound in a matter of days, rather than the months or years required for animal testing. Furthermore, the kits of this invention achieve these results for a fraction of the cost of animal testing and without the objectionable consequences to live animals. And, the diagnostic kits and methods of this invention yield direct information about the nature of a toxin's action on mammalian cells—something that the prior art short-term assays fail to do.

DETAILED DESCRIPTION OF THE INVENTION

Figure 1:
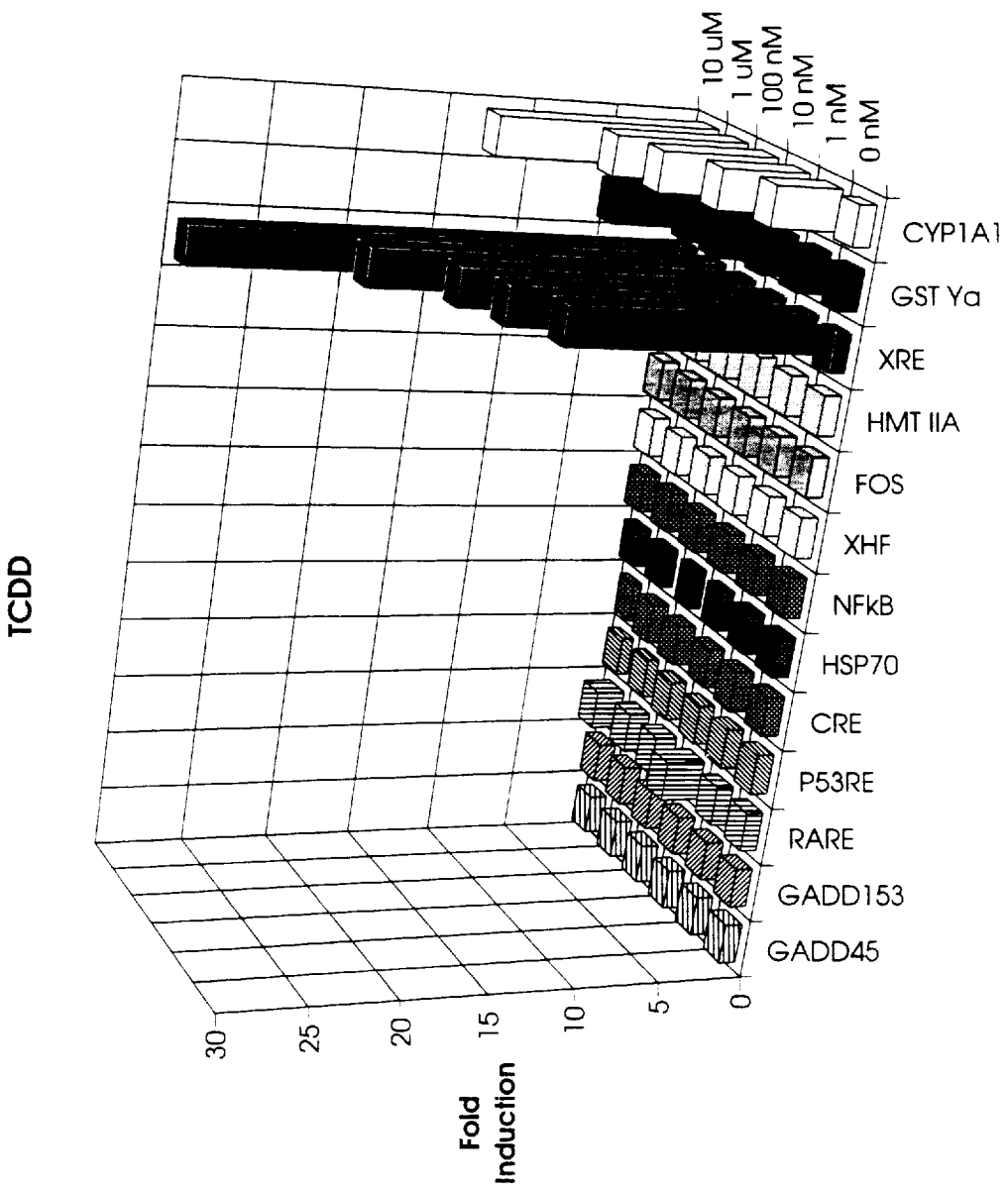
FIG. 1 depicts the relative expression of chloramphenicol acetyl transferase under the control of different stress promoters in the presence of varying concentrations of tetrachlorodibenzo-p-dioxin (TCDD).

As used herein, the terms "stress" and "toxicity" are used interchangeably and refer to the disturbance of the biochemical and biophysical homeostasis of the cell.

The term "redox stress", as used throughout this application, refers to conditions which vary from the normal reduction/oxidation potential ("redox") state of the cell. Redox stress includes increased levels of superoxides radicals, increased levels of peroxides—both hydrogen peroxide and organic peroxides—, decreased levels of glutathione and any other conditions which alter the redox potential of the cell, such as exposure to strong reducing agents, some aromatic hydrocarbons, electrophilic compounds, aldehydes, intracellular thiols, steroids, methyl cholanthrene, phenobarbital and $CCl_4$. The term also includes any additional conditions which cause proliferation of peroxisomes. The term "DNA stress", as used herein, refers to alterations to deoxyribonucleic acid or to precursor nucleotides. For example, DNA stress includes, but is not limited to, DNA strand breaks, DNA strand cross-linking, exposure to DNA intercalating agents, both increased and decreased superhelicity, oxidative DNA damage, DNA alkylation, oxidation of nucleoside triphosphates and alkylation of nucleoside triphosphates. The term also includes inhibition of DNA synthesis and replication and inhibition of mitosis or meiosis. And the term includes conditions caused by exposure to growth factors, interferons, tumor promoters, tumor necrosis factor, phorbol esters, hydrophobic cytotoxic drugs, inflammatory agents, mitogens, carcinogens, X-rays, UV radiation and dimethylnitrosamine. "Protein stress", as used throughout the application, refers to alterations to proteins or individual amino acids and inhibition of enzyme functions, as well as perturbations of intracellular transport of proteins. The term includes, but is not limited to, denaturation of proteins, misfolding of proteins, chelation of protein cofactors, cross-linking of proteins, both oxygen-dependent and -independent oxidation of inter- and intra-chain bonds, such as disulfide bonds, alkylation of proteins, oxidation of individual amino acids and protein damage caused by exposure to heavy metals, such as cadmium and heat.

I use the term "energy or ionic stress" to encompass conditions which affect ATP levels in the cell or ionic gradients across a cell membrane. Examples of energy stress are forced anaerobic metabolism in the presence of oxygen, perturbations of electron transport, exposure to uncoupling agents, membrane depolarization, osmotic shock, exposure to ions, such as $Ca^{2+}$, exposure to high levels of cAMP and exposure to ethanol.

The term "cell surface receptor-mediated stress" refers to those conditions which alter the transcription level of genes whose expression is regulated by the interaction of a cell surface receptor with a ligand. Examples of such stress include exposure of the skin, eyes or mucous membranes to irritants, allergens or inflammatory compounds.

The term "stress promoter induction" refers to conditions which increase the level of expression of a gene operably linked to a native stress promoter or a recombinantly derived stress promoter which contains a response element. The term "operative linkage", "operatively linked" or "operably linked" refers to the positioning of the promoter relative to the gene such that transcription of the gene is regulated by the promoter. The term encompasses both recombinant constructs, as well as the structure of a naturally occurring promoter and its associated gene.

The term "determining and characterizing the toxicity of a compound" includes identifying a compound as a toxin and elucidating its mechanism of action within the cell.

The term "nucleic acid sequences" as used in this application, includes RNA, single or double-stranded cDNA or portions thereof, single or double-stranded genomic DNA or portions thereof, or single or double stranded synthetic oligonucleotides.

Whereas every gene is controlled by a unique promoter, genes which respond to identical stresses contain a common response element within their promoters. Accordingly, the same response element is responsible for inducing expression of a family of genes upon exposure to a certain stress. When isolated and operably linked to a minimal promoter and a structural gene, the resulting construct functions like a stress promoter. This is particularly useful in dissecting a native stress promoter that responds to multiple stresses into its component parts.

Individual cells respond to toxic stimuli, in part, by activating specific genes whose protein products detoxify the stimuli or repair damage caused thereby. Eukaryotic cells have large number of genetic and biochemical responses to damage and stress. At least 50 different mammalian stress genes have already been isolated and characterized. These genes are induced by a variety of chemical and physical stresses or cellular damage.

Among the chemical stresses which induce one or more of these identified genes are exposure of the cell to mercury, heavy metals, nitroxides, aromatic hydrocarbons, acidity, basicity, alkylating agents, peroxidizing agents, cross-linking agents, ionophores, redox active agents, electrophilic compounds, inflammatory agents, hydrophobic cytotoxic drugs, ethanol, steroids, uncoupling agents, tumor promoters and cellular factors, such as tumor necrosis factor, growth factors and interferon. Physical stresses include exposure to UV radiation, heat or X-rays.

Examples of cellular damage which induce these identified genes are lipid oxidation, peroxisome proliferation, DNA strand breaks, DNA alkylation, DNA cross-linking, DNA oxidation, osmotic imbalance, protein oxidation, protein misfolding, protein alkylation, ATP depletion, membrane permeabilization, glutathione depletion and alterations in signal transduction. Many more stress genes are believed to exist. The identification and characterization of these additional stress genes is highly desirable in understanding what effects various chemical stresses have on the cell.

The present invention provides diagnostic kits and methods for determining and characterizing the toxicity of a compound in terms of the type of damage it causes within the cell, i.e., DNA damage, protein damage, redox damage, energy damage, ionic damage, etc. According to one embodiment, each diagnostic kit of this invention comprises a plurality of eukaryotic cells, each of which harbors at least one promoter or one promoter element which responds to stress. The plurality of cells, in toto, must comprise at least one promoter or promoter element which responds to each of the aforementioned types of stresses—redox, DNA, protein and energy/ionic—operably linked to a gene encoding a detectable product.

According to one embodiment, the plurality of cells in this kit are actually a single cell line, wherein each cell contains all of the different types of stress promoters and wherein each of those promoters is activated upon exposure to the appropriate stress. In this embodiment, the genes operatively linked to the stress promoters are most preferably the native stress genes. In this manner no genetic manipulation need be carried out on the cells prior to running an assay. In this preferred embodiment, the kits further comprise oligonucleotides or cDNAs which are complementary to at least a portion of either the coding or non-coding strand of the genes under control of the specific stress promoters. The oligonucleotides are used to detect and quantify the mRNA transcripts of those genes or the cDNA complements thereof, either of which may be the detectable product in this embodiment.

It should be noted that although all eukaryotic cells contain numerous stress promoters within their genomes, some of those promoters may or may not be activatable upon exposure to the proper stress. This is especially true in higher eukaryotes, such as mammals. Those cell lines whose stress promoters do respond to almost all of the appropriate stresses are preferred in the kits of this invention. These include primary tissue from mammalian liver, heart, lung, kidney, brain, or other organ, as well as mammalian derived cell lines established from these tissues available from American Type Culture Collection (ATCC, Rockville, Md.). More preferred are HepG2 cells, HeLa cells and WIL-2 cells. Most preferred are HepG2 cells.

The oligonucleotides employed in the above diagnostic kits and methods of this invention are chosen based upon their ability to specifically hybridize under relatively high stringency conditions to either the transcription product of the gene operatively linked to the various stress promoters or its complement (i.e., a single-stranded cDNA reverse transcribed from that mRNA). The choice of utilizing complementary or homologous oligonucleotides depends upon the method used for detecting the transcription products. These various methods are described later in the application.

Because the DNA sequences of many mammalian stress genes are known, hybridizable oligonucleotides are easily constructed. It should be noted that 100% homology or complementarity between the oligonucleotide and the stress gene mRNA is not required. This is because the oligonucleotide may be designed based upon the sequence of a stress gene from a species different from the source of the cells utilized in the kits and methods of this invention.

While it is expected that similar stress genes from different mammalian species will be closely related, the transcripts from those genes will most likely not have identical nucleotide sequences. Accordingly, the oligonucleotides utilized in the kits and methods of this invention are preferably at least 95% homologous or complementary. Preferably, the oligonucleotides are between 20 and 500 base pairs long. Most preferably, the oligonucleotides are between 50 and 100 base pairs.

More preferably, the oligonucleotides are synthesized using an oligonucleotide synthesizer, optionally followed by polymerase chain reaction ("PCR"). In this procedure, an oligonucleotide having a sequence identical to a portion of either the template strand or the non-coding strand and within the coding region of a known, sequenced stress gene is synthesized. If PCR is to be used to increase the quantity of oligonucleotide, the oligonucleotide is synthesized with an additional 6 to 12 nucleotides at each end. Those extra nucleotides serve as targets for complementary primers in a PCR reaction. Preferably the extra nucleotides at each end are complementary to one another. This allows a single primer to prime off of both the original oligonucleotide and the PCR product thereof. Most preferably, the extra nucleotides at each end are complementary homohexamers, i.e., AAAAAA at one end and TTTTTT at the other.

During PCR, one or more labeled nucleotides are preferably included in the polymerase reaction. Preferably the label is $^{32}$P, biotin or a fluorescent marker. This results in a labelled product that can be used directly to detect the level of transcription product. The advantage of this mixed oligonucleotide synthesizer/PCR technique is that microgram quantities of labelled oligonucleotide can be produced in a single procedure. The resulting oligonucleotides may optionally be biotinylated following synthesis and purification.

If the oligonucleotide is used to detect cDNA reverse transcripts of the transcription product, it is preferable that they not be labelled. In this embodiment, it is preferred that the label be incorporated into the cDNA, rather than the oligonucleotide.

The design of appropriate oligonucleotide probes for use in the kits and methods of this invention is relatively straightforward. Obviously, they should have high sequence similarity or complementarity to the stress gene mRNA to which they are designed to hybridize. The oligonucleotides in any particular kit should also have approximately the same melting temperature ($T_m$) so that a single warming apparatus (such as a water bath) may be utilized when carrying out hybridization and subsequent washing steps. Preferably the oligonucleotides are designed to have a $T_m$ of greater than 70° C. in 0.2X SSC. To determine which portions of the coding regions of the stress gene to use in designing oligonucleotide probes, one may utilize a commercially available computer program, such as OLIGO™ (National Biosciences, Plymouth, Minn.).

According to another embodiment, each of the plurality of eukaryotic cells in the diagnostic kit of this invention harbors a stress promoter or a stress response element which is operatively linked to a heterologous gene encoding a detectable product. In this embodiment, it is preferable that the same heterologous gene be linked to the various stress promoters or response elements in the kit. In this manner, only a single assay need be performed to detect induction of any of the stress promoters and stress response elements. It is also preferable that each cell within the kit contains only a single stress promoter or response element/heterologous gene construct. Thus, the expression of the detectable product in any given cell in the kit can be specifically correlated to the induction of a single stress promoter or response element.

The diagnostic kits and methods of this invention employ a plurality of eukaryotic cells, which, in toto, comprise promoters or response elements that respond to each of: redox stress, DNA stress, protein stress and energy stress. The preferred promoters and response elements of this invention for use with mammalian cells are listed below in Table 1.

TABLE 1

Preferred Mammalian Stress Promoters

| Promoter | Redox | DNA | Protein | Energy/Ionic |
|---|---|---|---|---|
| CYP1A1 | X | | | |
| GST Ya | X | X | | |
| GADD45 | | X | | |
| GRP78 | | X | X | X |
| JUN | X | X | X | |
| FOS | | X | X | X |
| XHF | | X | | |
| HSP70 | | | X | |
| MT IIA | X | | X | |
| GADD153 | | X | | |
| ALDH 1 | X | | | |
| HMO | X | X | | |
| CRE | | | | X |
| XRE | X | | | |
| NFkBRE | X | X | | |
| RARE | X | | | |
| ThRE | X | | | |
| PPRE | X | | | |
| TRE | | | X | |
| ERE | X | | | |
| p53RE | | X | | |

Preferably, the promoters or response elements which respond to redox stress in the methods and kits of this invention are selected from the promoters of the CYP1A1, GST Ya, JUN, ALDH1 and HMO genes and the XRE, NFkBRE, PPRE, RARE, ERE, and ThRE response elements.

The CYP1A1 gene encodes cytochrome P450 1A1, an enzyme involved in the metabolism of polycyclic aromatic hydrocarbons, such as benzo(a)pyrene. The gene is inducible by aromatic hydrocarbons, plant flavones and also by tetrachlorodibenzo-p-dioxin (TCDD), one of the most potent teratogens and tumor promoters [L. A. Neuhold et al., Mol. Cell. Biol., 9, pp. 2378–2386 (1989); Y. Fujii-Kuriyama et al., The FASEB J., 6, pp. 706–710 (1992); D. W. Nebert et al., Env. Health Perspec., pp. 13–25 (1990); R. A. Dixon et al., Biol. Rev., 61, pp. 239–241 (1986)]. The sequence of this gene is described in K. Sogawa et al., Proc. Natl. Acad. Sci. USA, pp. 8044–8048 (1986), the disclosure of which is herein incorporated by reference.

The GST Ya gene encodes the glutathione S-transferase Ya subunit, a unique xenobiotic-responsive element. The redox stress-sensitive portion of the GST Ya promoter is strongly induced by electrophilic herbicides, insecticides and planar aromatic hydrocarbons such as β-naphthoflavone and 3-methylcholanthrene [T. H. Rushmore et al., Proc. Natl. Acad. Sci. USA, 87, pp. 3826–3830 (1990)]. The sequence of this gene is described in T. H. Rushmore et al., supra, the disclosure of which is herein incorporated by reference.

The JUN oncogene codes for c-jun which participates in the formation of the AP-1 complex—a transcriptional activator. Redox stresses which activate the JUN gene are superoxide radicals and UVA radiation. The sequence of this gene is described in R. De Groot et al., EMBO J., 10, pp. 2523–2532 (1991), the disclosure of which is herein incorporated by reference.

The ALDH 2 gene encodes aldehyde dehydrogenase and is induced by aldehydes and peroxisome proliferators [D. W. Nebert, Env. Health Persp., 88, pp. 13–25 (1990)]. The sequence of that gene is described in L. C. Hsu et al., Proc. Natl. Acad. Sci. USA, 82, pp. 3771–3775 (1985), the disclosure of which is herein incorporated by reference.

The HMO gene codes for heme oxygenase. The promoter is induced by the following redox stresses: oxidative stress, hydrogen peroxides, and sodium arsenite [S. T. Keyse and R. M. Tyrell, Proc. Natl. Acad. Sci. USA, 86, pp. 99–103 (1989)]. The sequence of this gene is described in that document, the disclosure of which is herein incorporated by reference.

The XRE is a redox stress response element. It responds to xenobiotics, such as aromatic hydrocarbons [T. H. Rushmore et al., *Proc. Natl. Acad. Sci. USA*, 87, pp. 3826–3830 (1990)]. The sequence of this response element is described in that document, the disclosure of which is herein incorporated by reference.

NFkBRE is a redox stress response element which encodes a transcription factor that is activated by intracellular thiols [R. Schreck et al., *EMBO J.*, 10, pp. 2247–2258 (1991); B. Nelson et al., *Molec. Cell. Biol.*, 8, pp. 3526–3531 (1988)]. It also responds to DNA stress. The sequence of this response element is described in K. Leung and G. J. Nabel, *Nature*, 333, pp. 776–778 (1988), the disclosure of which is herein incorporated by reference.

PPRE is the peroxisome proliferation response element. It is a redox stress responsive element that is induced by peroxisome proliferators [C. Dreyer et al., *Cell*, 68, pp. 879–887 (1992)]. The sequence of this response element is described in that document, the disclosure of which is herein incorporated by reference.

RARE is the retinoic acid response element. It is a redox stress-sensitive response element that responds to the steroid hormone retinoic acid and its analogs [H. de The, et al., *Nature*, 343, pp. 177–180 (1990), the disclosure of which is herein incorporated by reference].

ERE is the estrogen response element. It responds to redox stress that is induced by estrogenic compounds. The sequence of the ERE is described in V. Kumar, et al., Cell, 55, pp. 145–156 (1988), the disclosure of which is herein incorporated by reference.

ThRE is the thyroid hormone response element. It responds to redox stress that is induced by thyroid hormone and its analogs. The sequence of the ThRE is described in M. Beato, *Cell*, 56, pp. 335–344 (1989), the disclosure of which is herein incorporated by reference.

Other promoters and response elements which respond to redox and can be utilized in the kits and methods of this invention may be selected from those listed in Table 2, below. In the brief description of each of these genes and response elements that follows, the document which discloses the DNA sequence of the particular gene is indicated in brackets. The disclosure of each of these documents is herein incorporated by reference.

UGT encodes a UDP-glucoronosyl transferase and its redox response is induced by 3-methyl cholanthrene [T. Iyanagi et al, *J. Biol. Chem*, 261, pp. 15607–14 (1986)]. CYP11B2 encodes a cytochrome P450 whose redox response is induced by steroids [T. Kawamoto et al., *Proc. Natl. Acad. Sci. USA*, 89, pp. 1458–62 (1992)]. Cu.ZnSOD encodes a superoxide dismutase that is induced by copper- and zinc-catalyzed superoxide formation [E. Danciger et al., *Proc. Natl. Acad. Sci. USA*, 83, pp. 3619–23 (1986)]. The MnSOD gene encodes a superoxide dismutase which can be activated by tumor necrosis factor, interleukin-2 and lipopolysaccharides [M. K. St. Clair and J. C. Holland, *Cancer Res.*, 51, pp. 939–943 (1991)]. ADPRT encodes a ribosyl transferase and is induced by oxidative stress. GP encodes glutathione peroxidase and its redox response is induced by peroxides [S. Chada, *Genomics*, 6, pp. 268–71 (1990)]. FAOxase encodes fatty acyl-CoA oxidase and is induced by peroxisome proliferators [S. Miyazawa et al., *J. Biol. Chem.*, 262, pp. 8131–37 (1987)]. PBE encodes a peroxisomal enoyl-CoA hydratase/3-hydroxyacyl CoA dehydrogenase bifunctional enzyme and is induced by peroxisome proliferators [J. K. Reddy et al., *Proc. Natl. Acad. Sci. USA*, 83, pp. 1747–51 (1986)]. PPAR encodes a peroxisome proliferator-activated receptor and is induced by peroxisome proliferators [C. Dreyer et al., *Cell*, 68, pp. 879–87 (1992)]. EH encodes an epoxide hydrolase which responds to redox stress caused by phenobarbital [R. K. Skoda et al., *J. Biol. Chem.*, 263, pp. 1549–54 (1988)]. CYP2B2 [J. S. Miles et al., *Nucl. Acids Res.*, 16, pp. 5783–95 (1988)], CYP2E1 [J. E. Freeman et al., *Biochem. J.*, 28, pp. 689–95 (1992)] and CYP3A3 [N. K. Spurr et al., GenBank Accession number X12387] encode three different cytochrome P450s. They are responsive to redox stress caused by phenobarbital (2B2), $CCl_4$ (2E1), and aflatoxin, cyclosporin, testosterone and nifedipine (3A3), respectively. The P450b gene encodes the cytochrome P450b which is induced by phenobarbital [C. M. Giachelli, et al., *J. Biol. Chem.*, 264, pp. 7046–7053 (1989)]. The P450d gene encodes cytochrome P450d, which is induced by polycyclic aromatic hydrocarbons, isosafrole, and 3-amino-1-5H-pyrido[4,3-b]indole (Trp-P-2) [K. Sogawa et al., *J. Biol. Chem.*, 260, pp. 5026–5032 (1985)]. PPa encodes a poly (ADP-ribose) polymerase and has a redox stress-sensitive component which responds to lipid peroxidation and oxidative stress [K. Uchida et al, *Biochem. Biophys. Res. Comm.*, 148, pp. 617–22 (1987)]. PKC encodes protein kinase C and its redox stress-sensitive component is induced by lipid peroxidation. ALDH1 encodes another aldehyde dehydrogenase that is induced by aldehydes and peroxisome proliferators [L. C. Hsu et al., *Proc. Natl. Acad. Sci. USA*, 82, pp. 3771–75 (1985)]. The NMO1 gene encodes the-NAD(P)H menadione oxidoreductase and is induced by various xenobiotics including planar aromatic compounds, azo dyes and phenolic antioxidants [L. V. Favreau and C. B. Pickett, *J. Biol. Chem.*, 266, pp. 4556–4561 (1991)]. The GST2 gene encodes glutathione S-transferase-2 and responds to similar redox stresses as GST Ya [P. G. Board et al., *Proc. Natl. Acad. Sci. USA*, 84, pp. 2377–81 (1987)]. The GAPDH gene encodes glyceraldehyde-3-phosphate dehydrogenase [L. Ercolani et al., *J. Biol. Chem.*, 263, pp. 15335–41 (1988)]. The NQO gene encodes NAD(P)H quinone oxidireductase and responds to the same redox stresses as NMO [A. K. Jaiswal, *Biochemistry*, 30, pp. 10647–53 (1991)].

The promoters and response elements which respond to DNA stress that are useful in the methods and kits of this invention are preferably selected from the promoters of the GST Ya, GADD45, JUN, FOS, XHF and GADD153 genes and the TRE and p53RE response elements.

The GST Ya gene is described above. Its DNA stress-sensitive component is induced by alkylated DNA.

The GADD45 gene encodes a growth arrest and DNA damage responsive protein. The GADD4S gene is induced by UV irradiation, X-rays, and the DNA damaging agent, methyl methane sulfonate (MMS). This gene is described in Q. Zhan et al., *Mol. Cell Biol.*, 13, pp. 4242–50 (1993), the disclosure of which is incorporated by reference.

The JUN gene has a DNA stress-sensitive component that is induced by UVA radiation, tumor promoters and growth factors.

The FOS gene encodes the oncogene c-fos. The DNA stress-sensitive components of its promoter are induced by tumor promoters and growth factors [E. M. Haliday, *EMBO J.*, 10, pp. 109–115 (1991)]. The sequence of this gene is described in F. van Straaten et al., *Proc. Natl. Acad. Sci. USA*, 80, pp. 3183–3187 (1983), the disclosure of which is incorporated herein by reference.

The XHF gene codes for collagenase and is activated by mitogenesis, inflammatory agents, UV radiation, and also in response to the tumor promoter, 12-O-tetradecanoylphorbol-13-acetate (TPA). The sequence of this gene is described in P. Angel et al., *Mol. Cell. Biol.,* 7, pp. 2256–2266 (1987), the disclosure of which is herein incorporated by reference.

The GADD153 gene is expressed in response to growth arresting signals and DNA damaging agents [J. D. Luethy and N. J. Holbrook, *Cancer Res.,* 52, pp. 5–10 (1992)]. The sequence of this gene is described in A. J. Fornace et al., *Mol. Cell. Biol.,* 9, pp. 4196–4203 (1989), the disclosure of which is herein incorporated by reference.

TRE is the TPA response element. It responds to DNA stress induced by phorbol esters. The sequence of TRE is described in P. Angel et al., *Cell,* 55, pp. 875–85 (1988), the disclosure of which is herein incorporated by reference.

p53RE is the p53 response element. It is responsive to DNA stress and is induced by X-rays and MMS. The sequence of the p53RE is described in Q. Zahn, et al., *Mol. Cell. Biol.,* 13, pp. 4242–4250 (1993), the disclosure of which is herein incorporated by reference.

Other promoters which respond to DNA stress and are useful in the methods and kits of this invention are listed in Table 2, below. In the brief description of each of these gene that follows, the document which discloses the DNA sequence of the particular gene is indicated in brackets. The disclosure of each of these documents is herein incorporated by reference.

The EGR-1 gene encodes an early growth response factor and is induced by mitogenesis and phosphatase inhibitors [S. V. Suggs, *Nucl. Acids Res.,* 18, pp. 4283–89 (1990)]. The GAS 2,3 gene is a gene which responds to growth arrest [C. Schneider et al., *Cell,* 54, pp. 787–793 (1988)]. The MGMT encodes an O-6-methylguanine methyltransferase and is induced by alkylated DNA [K. Tano et al., *Proc. Natl. Acad. Sci. USA.,* 87, pp. 686–90 (1990)]. DNA Pol encodes DNA polymerase A and is induced by mitogens. TK (which encodes thymidine kinase) [H. D. Bradshaw Jr. et al., *Mol. Cell. Biol.*], 4, pp. 2316–20 (1984).], DHFR (which encodes dihydrofolate reductase) [C. Morandi, *J. Mol. Biol.,* 156, pp. 583–607 (1982)] and PCNA (which encodes proliferating cell nuclear antigen) [D. Jaskulski et al., *J. Biol. Chem.,* 263, pp. 10175–79 (1988)] each are induced by cell proliferation. PGHS encodes prostaglandin endoperoxidase synthase and is induced by mitogens [S. A. Kraemer et al., *Arch. Biochem. Biophys.,* 293, pp. 391–400 (1992)]. LOX encodes a 5/12-lipoxygenase and is activated by exposure to tumor necrosis factor [P. A. Dixon et al., *Proc. Natl. Acad. Sci. USA,* 85, pp. 416–20 (1988)]. ISG15, which is an interferon-stimulated gene, is induced by α-interferon [N. Reich et al., *Proc. Natl. Acad. Sci. USA,* 84, pp. 6394–98 (1987)]. 2'-5' AS, which encodes 2'-5' oligoadenylate synthetase, is induced by β-interferon [M. Walthelet et al., *FEBS Lett.,* 196, pp. 113–20 (1986)]; EH, which is discussed above, contains a DNA stress-sensitive component which is activated by carcinogens. CYP2E1 contains a DNA stress-sensitive element which responds to dimethylnitrosamine. TPO1 and TPO2 encode topoisomerases and are induced by DNA strand breaks and agents which cause promoter recombination [P. D'arpa et al., *Proc. Natl. Acad. Sci. USA,* 85, pp. 2543–47 (1988); M. Tsai-Pflufelder et al., *Proc. Natl. Acad. Sci. USA,* 85, pp. 7177–81 (1988)]. PPa, which was also discussed above, responds to DNA stress caused by DNA damage. DRA encodes HLA class II and is induced by interferon gamma [A. J. Korman et al., *Proc. Natl. Acad. Sci. USA,* 79, pp. 6013–17 (1982); D. A. Shackelford et al., *Immunol. Rev.,* 66, pp. 133–187 (1982)]. The MnSOD promoter, which is described above, also contains a DNA stress-responsive element that is induced by tumor necrosis factor. The MDR-1 gene encodes a protein which imparts multidrug resistance and is mainly induced by hydrophobic cytotoxic drugs [J. A. Silverman et al., *Gene,* 106, pp. 229–236 (1991)]. The beta-pol gene encodes the DNA repair enzyme DNA polymerase beta and responds to N-methyl-N'-nitro-N-nitrosoguanidine (MNNG), mechlorethamine hydrochloride; and (HN2), and cis-platinum(II) diamine dichloride (cis-Pt) [S. G. Widen, et al., *J. Biol. Chem.,* 263, pp. 16992–98 (1988)]. The stromelysin-1 gene encodes a protein that is induced by phorbol esters, such as PMA [K. L. Sirum et al., *Biochemistry,* 28, pp. 8691–98 (1989)]. The PCNA gene encodes proliferating cell nuclear antigen which is induced by tumor promoters [S. Travali et al., *J. Biol Chem.,* 264, pp. 7466–72 (1989)].

Promoters which respond to protein stress useful in the methods and kits of this invention are preferably selected from GRP78, JUN, FOS, HSP70 and MTIIA.

The GRP78 gene encodes a 78-kDa protein that is a major endoplasmic reticulum component. GRP78 is induced by misfolded proteins and glycosylation blocks [S. K. Wooden, et al., *Mol. Cell. Biol.,* 11, pp. 5612–23 (1991)]. The sequence of this gene is described in E. Resendez et al., *Mol. Cell. Biol.,* 5, pp. 1212–19 (1985), the disclosure of which is herein incorporated by reference.

JUN and FOS, which are described above, both contain protein stress-responsive elements that are induced by heat.

The HSP70 gene encodes the heat shock protein 70 and is induced by heat, denatured proteins, amino acid analogues, heavy metals, anoxia and inhibitors of energy metabolism [D. D. Mosser et al, *Mol. Cell. Biol.,* 8, pp. 4736–44 (1988)]. The sequence of this gene is described in C. Hunt and R. I. Morimoto, *Proc. Natl. Acad. Sci USA,* 82, pp. 6455–59 (1985), the disclosure of which is herein incorporated by reference.

MT IIA, which encodes metallothionine IIA, is induced by heavy metals and glucocorticoids [M. Karin et al., *Nature,* 299, pp. 797–802 (1982)]. The sequence of that gene is described in the above reference, the disclosure of which is herein incorporated by reference.

Other promoters which may be employed in the kits and methods of this invention to detect protein stress may be selected from those promoters listed in Table 2, below, which respond to protein stress. In the brief description of each of these gene that follows, the document which discloses the DNA sequence of the particular gene is indicated in brackets. The disclosure of each of these documents is herein incorporated by reference.

MT 1A [R. I. Richards et al, *Cell,* 37, pp. 263–72 (1984)] and MT III [R. D. Palmitter et al., *Proc. Natl. Acad. Sci. USA,* 89, pp. 6333–37 (1992)] each encode a metallothionein gene that is induced by the heavy metal, cadmium. GP contains an element that responds to the protein damaging heavy metal, selenium.

The preferred promoters and response elements which respond to energy/ionic stress in the methods and kits of this invention are the promoters of the FOS and GRP78 genes and the CRE response element.

FOS, which is described above, contains the cAMP response element ("CRE") [W. J. Roesler et al., *J. Biol. Chem.,* 263, pp. 9063–9066 (1988)].

GRP78, which is also described above, contains an energy or ionic stress responsive element that responds to calcium ionophores.

CRE is the cAMP response element. It is an energy/ionic stress-sensitive response element which responds to increased levels of cAMP [J. Roesler et al., *J. Biol. Chem.*, 263, pp. 9063–66 (1988), the disclosure of which is herein incorporated by reference.]

Other energy or ionic stress promoters that may be employed in the kits and methods of this invention are listed in Table 2, below. In the brief description of each of these gene that follows, the document which discloses the DNA sequence of the particular gene is indicated in brackets. The disclosure of each of these documents is herein incorporated by reference.

Two cytochrome P450 genes—CYP11B2 which is induced by cAMP; and CYP2E1, which is induced by ethanol—contain energy or ionic stress responsive elements. 2'-5' AS contains an element which responds to energy or ionic stress induced by ethanol. DBH, which encodes dopamine β-hydroxylase [B. Grima, *Nature*, 326, pp. 707–11 (1987)] and TH, which encodes tyrosine hydroxylase [A. Lamouroux et al., *EMBO J.*, 6, pp. 3921–37 (1987)] are both induced by membrane depolarization. ODC, which encodes ornithine decarboxylase, is induced by osmotic shock [N. J. Hickok et al., *DNA*, 6, pp. 179–87 (1987)]. G6PD encodes glucose-6-phosphate dehydrogenase and is induced by ATP depletion. PKC contains an energy or ionic stress-responsive element which is induced by Na/K ATPase depletion. PVALB encodes parvalbumin and is induced by calcium ions [C. Lutum et al. GenBank Accession number X63070]. Stromelysin-1 contains an energy or ionic stress-responsive element which is induced by calcium ionophores.

TABLE 2

Other Mammalian Stress Promoters

| Promoter | Redox | DNA | Protein | Energy/Ionic |
| --- | --- | --- | --- | --- |
| UGT | X | | | |
| CYP11B2 | X | | | X |
| Cu.ZnSOD | X | | | |
| MnSOD | X | X | | |
| NMO 1 | X | | | |
| ALDH 2 | X | | | |
| ADPRT | X | | | |
| GP | X | | X | |
| GAS 2,3 | | X | | |
| EGR-1 | | X | | |
| MGMT | | X | | |
| DNA Pol | | X | | |
| beta-pol | | X | | |
| DHFR | | X | | |
| TK | | X | | |
| PCNA | | X | | |
| PGHS | | X | | |
| LOX | | X | | |
| ISG15 | | X | | |
| DRA | | X | | |
| MDR-1 | | X | | |
| 2'-5' AS | | X | | X |
| FAOxase | X | | | |
| PBE | X | | | |
| PPAR | X | | | |
| Mt 1A/IIIA | | | X | |
| TH | | | | X |
| DBH | | | | X |
| ODC | | | | X |
| EH | X | X | | |
| CYP2B2 | X | | | |
| CYP2E1 | X | X | | X |
| CYP3A3 | X | | | |
| P450b | X | | | |
| P450d | X | | | |
| TPO1/TPO2 | | X | | |
| PPa | X | X | | |
| G6PD | | | | X |
| PKC | X | | | X |

TABLE 2-continued

Other Mammalian Stress Promoters

| Promoter | Redox | DNA | Protein | Energy/Ionic |
| --- | --- | --- | --- | --- |
| PVALB | | | | X |
| Stromelysin-1 | | X | | X |
| GST2 | X | | | |
| GAPDH | X | | | |
| NQO | X | | | |
| PCNA | | X | | |
| ARE | X | | | |

Because response elements can only be isolated from the promoters which contain them by recombinant DNA methods, the use of such elements in the kits and methods of this invention is limited to embodiments utilizing promoter-heterologous gene constructs.

In order to operatively link a response element to a heterologous gene, it must first be ligated to a minimal promoter. A minimal promoter is one which constitutively causes a basal expression of a gene operatively linked thereto. Preferred minimal promoters are the SV40 minimal promoter, the TK minimal promoter or the β-interferon minimal promoter. These minimal promoters are well known in the art. This minimal promoter/response element construct is then operatively linked to the heterologous gene by well-known recombinant DNA methods.

Many of the above described promoters, or functional equivalents thereof, are present in other eukaryotes, such as nematodes, yeast, insects, reptiles, amphibians and plants.

For example, yeast contain a metallothionein gene, CUP, that responds to protein stress induced by exposure to heavy metals [T. R. Butt et al., *Gene*, 27, pp. 23–33 (1984); T. R. Butt et al., *Proc. Natl. Acad. Sci. USA*, 81, pp. 3332–36 (1984)]. Yeast also contain equivalents of the HSP70 and GRP 78 genes [E. A. Craig, In *Stress Proteins In Biology And Medicine*, Cold Spring Harbor Laboratory Press, Cold Spring Harbor, New York, pp. 301–21 (1990); W. R. Boorstein et al., *J. Biol. Chem.*, 265, pp. 18912–21 (1990); and M. D. Rose et al., *Cell*, 57, pp. 1211–21 (1990)]. Alcohol dehydrogenases, a family of yeast genes that are induced by alcohol, an energy/ionic stress have also been sequenced [T. Young et al., *Basic Life Sci.*, 19, pp. 335–361 (1982)].

Also, a large number of DNA stress genes have been identified and sequenced in yeast. These include MAG, the methyladenine DNA glycosylase, and MGT1, which respond to DNA alkylation damage [W. Xiao et al., *Mol. Cell. Biol.*, 13, pp. 7213–21 (1993)]; RAD51, RAD54, RAD6, RAD23, RAD2, RAD18 and RAD7, all of which respond to DNA strand breaks [G. Basile et al., *Mol. Cell. Biol.*, 12, pp. 3235–46 (1992); G. M. Cole et al., *Mol. Cell. Biol.*, 9, pp. 3314–3326 (1989); K. Madura et al., *Nucleic Acids Res.*, 18, pp. 771–78 (1990); *Nucleic Acids Res.*, 18, pp. 4737–42 (1990); K. Madura et al., *J. Bacteriol.*, 166, pp. 914–23 (1990); J. S. Jones et al., *Nucleic Acids Res.*, 19, pp. 893–98 (1991); J. S. Jones et al., *Nucleic Acids Res.*, 18, pp. 3281–85 (1990)]; PHR1 which is induced by DNA damaging agents [J. B. Sebastion et al., *Mol. Cell. Biol.*, 10, pp. 4630–37 (1990)]; RNR2 and RNR3, the yeast ribonucleotide reductases, which are induced by DNA damage [S. J. Elledge et al., *Mol. Cell. Biol.*, 9, pp. 5373–86 (1989); S. J. Elledge et al., *Gene Dev.*, 4, pp. 740–51 (1990); Z. Zhou et al., *Genetics*, 131, pp. 851–66 (1992)]; CDC9, the yeast DNA ligase [T. A. Peterson et al., *Mol. Cell. Biol.*, 5, pp. 226–35 (1985)]; UBI4, another gene that responds to DNA damage [J. M. Treger et al., *Mol. Cell. Biol.*, 8, pp. 1132–36 (1988)]; and DDR48, a gene which responds to mutagens [J. M. Treger et al., *Mol. Cell. Biol.*, 10, pp. 3174–84 (1990)]. In addition, several other DNA stress genes have also been identified in yeast [G. W. Robinson et al., *Proc. Natl. Acad. Sci. USA*, 83, pp. 1842–46 (1986); S. W. Ruby et al., *Mol. Cell. Biol.*, 5, pp. 75–84 (1985); E. C. Friedberg, *Microbiol. Rev.*, 52, pp. 70–102 (1988); T. McClanahan et al., *Mol. Cell. Biol.*, 4, pp. 2356–2363 (1984)].

The appropriate combination of any or all of these promoters, as well as other known yeast stress promoters, may be utilized in the methods and kits of this invention. It will be understood that if yeast stress promoters are employed, yeast hosts are preferred and should be grown under conditions appropriate for such a host. Such conditions are well known in the art.

The most preferred kits and methods which utilize oligonucleotides to detect toxicity comprise the following stress promoters: ALDH1, CYP1A1, FOS, GADD153, HMO, HSP70, JUN and MTIIA. The most preferred kits and methods which utilize reporter gene expression to detect toxicity comprise the following stress promoters and response elements: CYP1A1, GST Ya, GADD45, FOS, XHF, HSP70, MT IIA, GADD153, CRE, XRE, NFkBRE, RARE and p53RE.

According to another embodiment of this invention, the diagnostic kits and methods additionally employ at least one cell surface receptor-mediated stress promoter. Such kits and methods are particularly useful for determining and characterizing the toxicity of a compound on external organs, such as skin, the eye or mucous membranes. The use of cell surface receptor-mediated stress promoters allows for the detection of compounds which can cause local irritation or inflammation of such external organs.

Irritants and inflammatory agents may cause sub-lethal cell injury that cannot be detected histologically. Such toxins would not be toxic to an animal as a whole in a classic sense and thus may escape detection by methods such as live animal testing. The use of cell surface receptor-mediated stress promoters in the kits and methods of this invention allow for the detection and characterization of such local irritants or inflammatory agents, as well as the ability to distinguish between the two on a subcellular level—something that whole animal testing cannot achieve.

The preferred cell surface receptor-mediated stress promoters for use in such kits are selected from the promoters of the IL-1 alpha, G-CSF, GM-CSF, TNF-alpha, IL-3, IL-6, IL-8, ICAM-1 and stromelysin-1 genes.

The Interleukin (IL)-1 alpha gene encodes a cytokine that is induced by mitogens, lipopolysaccharide (LPS), PMA, silica, other cytokines, and UVB irradiation [T. A. Luger et al., *J. Invest. Dermatol.*, 95, pp. 100S–104S (1990)]. The sequence of that gene is described in Y. Furutani et al., *Nucleic Acids Res.*, 14, pp. 3167–79 (1986), and the disclosure of which is herein incorporated by reference.

The granulocyte colony stimulating factor (G-CSF) gene produces a protein that is induced by endotoxin, interferons, and PMA [T. A. Luger et al., *J. Invest. Dermatol.*, 95, pp. 100S–104S (1990)]. The sequence of this gene is described in S. Nagata et al., *EMBO J.*, 5, pp. 575–581 (1986), the disclosure of which is herein incorporated by reference.

The granulocyte macrophage colony stimulating factor (GM-CSF) gene encodes a protein that is produced in response to the same stimuli as G-CSF (T. A. Luger et al., supra). The sequence of this gene is described in S. Miyatake et al., *EMBO J.*, 4, pp. 2561–2568 (1985), the disclosure of which is herein incorporated by reference.

The tumor necrosis factor (TNF) alpha gene encodes a protein that is induced by IL-1 alpha and IFN gamma [B. J. Nickoloff et al., *J. Invest. Dermatol.*, 94, pp. 151S–157S (1990)]. The sequence of this gene is described in D. Semon et al., *Nucleic Acids Res.*, 15, pp. 9083–9084 (1987), the disclosure of which is herein incorporated by reference.

The IL-3 gene encodes a product of the same name and is induced by interferon (IFN) gamma, PMA, and UVB irradiation [T. A. Luger et al., supra]. The sequence of that gene is described in D. R. Cohen et al., *Nucl. Acids Res.*, 14, pp. 3641–58 (1986), the disclosure of which is herein incorporated by reference.

The IL-6 gene produces a protein that is expressed in response to other cytokines, bacterial toxins, viruses, tumor promoters and sodium lauryl sulphate [T. Hunziker et al., *Brit. J. Dermatol.*, 127, pp. 254–57 (1992) and T. A. Luger et al., J. Invest. Dermatol., 95, 100S–104S (1990)]. The sequence of this gene is described in K. Yasukawa et al., *EMBO J.*, 6, pp. 2939–45 (1987), the disclosure of which is herein incorporated by reference.

The IL-8 gene is induced by the cytokines IL-1 alpha, tumor necrosis factor (TNF-alpha), and IFN-gamma, as well as by LPS, and tumor promoters [I. C. Oliveira et al., *Proc. Natl. Acad. Sci. USA*, 89, pp. 9049–53 (1992)]. The sequence of that gene is described in N. Mukaida et al., *J. Immunol.*, 143, pp. 1366–71 (1989), the disclosure of which is herein incorporated by reference.

The intracellular adhesion molecule (ICAM)-1 gene encodes a protein that is induced by cytokines, LPS, hydrocortisone, and PMA [S. W. Caughman et al., *J. Invest. Dermatol.*, 98, pp. 61S–65S (1992)]. The sequence of this gene is described in B. G. Stade et al., *Immunobiology*, 181, pp. 851–56 (1990), the disclosure of which is herein incorporated by reference.

The stromelysin-1 gene contains a cell surfaced receptor-mediated stress element that is induced by epidermal growth factor.

Other cell surface receptor-mediated stress promoters that may be utilized in the kits and methods of this invention include the promoters of IL-1 beta, TGF-alpha, IL-10 and M-CSF genes, as well as the promoters of the genes that encode the cell surface receptor that regulates the expression of any of the above genes. In the brief description of each of these gene that follows, the document which discloses the DNA sequence of the particular gene is indicated in brackets. The disclosure of each of these documents is herein incorporated by reference.

The IL-1 beta gene is induced by the same agents as the IL-1 gene alpha [J. J. Huang et al., *J. Immunol.*, 140, pp. 3838–43 (1988)]. The transforming growth factor (TGF) alpha gene encodes a protein that is induced by itself as well as by IFN-gamma [F. Iris et. al., *Nature Genetics*, 3, pp. 137–45 (1993)]. IL-10 is induced by contact allergens such as trinitrochlorobenzene (TNCB) and haptens [J. M. Kim et al., *J. Immunol.*, 148, pp. 3618–23 (1992)]. The other cell surface receptor-mediated stress genes have also been described in the art.

The diagnostic kits and methods of this invention rely on the induction of specific stress promoters or stress response elements and the transcription and/or translation of a gene operatively linked thereto.

For embodiments of the invention that employ a heterologous gene operatively linked to a mammalian stress promoter or stress responsive element, the choice of gene is essentially limitless. The only parameters that are required are (1) that a DNA sequence encoding the assayable product has been characterized; and (2) that the product of the gene can be detected. Sufficient characterization includes knowledge of the entire coding sequence, availability of a genomic clone or knowledge of a sufficient number of restriction sites within the genomic DNA sequence to allow the gene to be manipulated so as to create an operative linkage to the stress promoter.

Promoters of most mammalian stress genes are inducible by more than one type of stress. This is because such promoters contain within their sequence a number of stress response elements, each of which is responsive to a different type of stress. In embodiments that utilize such multiple stress promoters it is preferable that another promoter which responds to only one of the multiple stresses also be employed. This is true whether native promoter-gene systems or recombinant promoter-assayable gene fusions are used. For example, the HMO promoter and the JUN promoter are induced by both peroxides and by UVA rays. Thus, these promoters respond to both redox stress and DNA stress. An NMO1 promoter, which responds solely to oxidative stress, may be used together with an HMO or JUN promoter. This combination of promoters allows one to determine whether induction of the multiple stress promoter was due to redox stress or UVA light. In this manner, the nature of the stress caused by a compound can be more accurately determined.

According to another embodiment of this invention, individual response elements of a promoter may be isolated and then operatively linked to a mammalian minimal promoter and to a gene which encodes a detectable product. Thus, expression of the detectable product in the presence of a compound is correlated with only one particular type of stress.

In embodiments which employ a gene encoding a detectable product, the assayable product is preferably β-galactosidase (encoded by the lacZ gene), chloramphenicol acetyl transferase (encoded by the CAT gene), galactose kinase (encoded by the galK gene), β-glucosidase (encoded by the gus gene), glutathione transferase, human growth hormone (encoded by the hGH gene) or firefly luciferase (encoded by the lux gene). Most preferably, the CAT gene is employed.

The stress promoter-assayable product fusions harbored by the hosts employed in certain of the diagnostic kits and methods of this invention may be made using standard recombinant DNA techniques that are well known in the art. The choice of techniques depends upon what is known about the particular stress promoter to be used in the strain.

If a genomic fragment containing a stress promoter and its gene have been isolated or cloned into a vector, the promoter is removed by appropriate restriction enzyme digests. The promoter fragment is then isolated and operably linked to a gene encoding an assayable product in a plasmid. The vector should also contain a marker, such as Neo, for identifying stable transfectants. Screening for a functional fusion is achieved by exposing transfectants to a stress which is known to induce the specific stress promoter and assaying for the detectable gene product.

If the nucleotide sequence of the stress promoter and its gene is known, polymerase chain reaction technology may be employed to produce assayable protein fusions. Specifically, one synthesizes primers which are complementary to the 5' and 3' ends of the stress promoter portion of the gene, hybridizes those primers to denatured, total mammalian DNA under appropriate conditions and performs PCR. In this manner, clonable quantities of any sequenced stress promoter may be obtained. Once the stress promoter DNA has been obtained, it is operatively linked to a DNA encoding an assayable protein in an appropriate vector, as described above. Such methods are well-known in the art.

Constructing operable fusions of stress promoter response elements to a gene encoding a detectable product is also carried out by standard recombinant DNA techniques. Because response elements are small, DNA encoding them may be produced using an oligonucleotide synthesizer. Oligonucleotides corresponding to both strands of the response element are synthesized, annealed together and cloned into a plasmid containing a reporter gene under control of a minimal promoter. Alternatively, the double stranded oligonucleotides can be allowed to multimerize via self ligation prior to insertion into a vector. The multiple copies of the response element allow for higher expression of the detectable product upon stress induction.

Embodiments of the present invention that employ native stress genes as the genes encoding an assayable product require no genetic manipulation prior to assaying toxicity.

The choice of cell line to use in the kits and methods of this invention is dependent upon the assay to be used to determine toxicity. For those embodiments which utilize stress promoter-assayable product gene fusions, the cells must be able to produce the expression product in assayable form. Moreover, those cells should not constitutively produce the assayable product from another copy of the gene in their genome.

For embodiments which utilize the cell's native stress genes, the choice of cells is based upon the ability of those genes to be induced by stress. Preferred cells for embodiments that do not employ cell surface receptor-mediated stress promoters are HeLa, HepG2 and WIL-2. For those kits and methods that do employ cell surface receptor-mediated stress promoters, the preferred cell line is one derived from the organ of concern. For example, if the stress kits and methods are intended to identify compounds which affect the skin, a skin fibroblast or keratinocyte cell line, such as SCC12 or its derivatives, such as C6C1, is preferred. For kits and methods seeking to identify toxins to the eye, a corneal cell line is most preferred.

When utilizing stress promoter-assayable product fusions, it is preferable that each host employed in the kits and methods of this invention harbors only one such fusion. In this manner, if a compound induces expression of the assayable gene product in any particular host cell, the specific type of stress caused by the compound can unambiguously be identified.

It is known that some compounds are not toxic to mammals in their native form, but become toxic after being processed by the liver. Therefore, according to another embodiment of this invention, the compound to be tested in the methods and kits of this invention is pre-treated with an S9 liver extract. Methods for preparing an S9 liver extract ("S9") are described by S. Vennitt et al., In *Mutagenicity Testing—A Practical Approach,* S. Vennitt et al., eds., IRL Press, Oxford, England, pp. 52–57 (1984), the disclosure of which is herein incorporated by reference. S9 is generally a crude homogenate of rat liver with insoluble particles removed by low speed centrifugation, but may also be prepared from human or other mammalian liver. S9 is incubated with the test compound in a potassium buffer containing NAD(P)H to mimic stage I and stage II biotransformation of compounds normally performed by the mammalian liver prior to performing the toxicity assay. If, however, primary mammalian liver cells are utilized in the kits and methods of this invention, S9 pre-treatment is unnecessary. The cells will be capable of performing stage I and II biotransformation of compounds under assay growth conditions.

Alternatively, the cells utilized in the kits and methods of this invention are co-cultured with cells capable of performing stage I and II biotransformation, preferably, a primary liver cell line. The biotransformation of the compound being assayed is, in this instance, performed by those other cells, rather than enzymatic fractions derived from liver cells.

Prior to carrying out an assay on a compound of unknown toxicity using the methods and kits of this invention, standard curves should be generated utilizing at least one and preferably at least three compounds that are known to induce each specific stress promoter or response element that will be used to screen the unknown compound.

Each known chemical should more preferably be tested against all of the promoters, not just the promoter that it is known to induce. And each chemical should be assayed over a sufficiently wide range of concentrations to provide a useful standard curve, preferably 1 picomolar to 1 millimolar as well as at several time points.

Once the standard curves have been generated, a computer data base containing those curves is generated. This database is then used to compare stress promoter-induction profiles of the compounds to be tested with those of the known toxins used to generate the standard curve. Thus, the results for any untested compound are expressed in terms of relative toxicity compared to known inducers of stress promoters.

Each of the characterization and toxicity determination methods of this invention comprise the first step of culturing the cells both prior to and following exposure to a potential toxic compound. Culture conditions will vary depending upon the cell type utilized. Most preferably, immortalized human liver cells (HepG2) are used. Growth of these cells is performed under standard tissue culture conditions— minimal essential medium at 37° C., 5% $CO_2$. The cells are routinely grown in 165 $cm^2$ flasks until they reach a density of about $5\times10^6$ cells/ml.

Following this initial growth, the cells are subcultured and exposed to the compound to be tested. A typical assay employs approximately $2.75\times10^5$ cells/ml. For initial tests on a compound, a series of 10-fold dilutions of the compound should be used. Another series of dilutions of the compound which have been pre-incubated with S9 fraction should also be prepared and added to a second portion of each culture. A third portion of each culture, which serves as a control, is not exposed to the compound, but otherwise treated in the same manner as described below.

All of the cultures are then allowed to incubate at normal growth temperature for a period of time ranging from 5 minutes to 48 hours. More preferably, exposure to the toxic or test compound is for about 2 to 32 hours. Following exposure to the test compound, the level of assayable product or stress gene mRNAs are measured.

If the embodiment measuring assayable product is employed, quantification may be carried out in a number of ways that are well known in the art. For example, a calorimetric substrate may be utilized if the expression product is an enzyme. Appropriate colorimetric substrates for specific enzymes are well-known in the art. Alternatively, an assay which employs specific antibodies, such as an RIA or ELISA, can be used to detect the expression product.

Depending upon the nature of the assay used, the buffer conditions of the lysed culture or supernatant may need to be adjusted. Accordingly, suitable buffer may be added to the lysed culture or supernatant so that optimal conditions for the particular assay are obtained. For example, if the assayable product is to be detected by an RIA or ELISA assay, the buffer conditions must be adjusted to a neutral pH to allow for maximal antibody-antigen complex formation and to minimize non-specific antibody binding. Such conditions are well known in the art and are exemplified by a final buffer condition of 50 mM phosphate buffer, 150 mM NaCl, pH 7.0. If the assayable product is an enzyme and detection is to be achieved by a calorimetric substrate assay, buffer conditions must be optimized for maximal enzymatic activity and minimal non-catalytic cleavage of the substrate. These conditions are conventional and vary depending on the enzyme to be assayed.

In the most preferred embodiment of this aspect of the invention, the detectable product is chloramphenicol acetyl transferase (CAT). Assays for this enzyme are well-known in the art and are described in J. Sambrook et al., "Molecular Cloning—A Laboratory Manual, Second Edition", Cold Spring Harbor Laboratory Press, pp. 16.60–16.65 (1989), the disclosure of which is herein incorporated by reference. That reference also describes assays for β-galactosidase, another assayable product useful in the methods and kits of this invention (pp. 16.66–16.67).

In embodiments that utilize transcription level to determine stress gene induction, the level of mRNA transcribed from genes operatively linked to the stress promoters utilized in the kits and methods of this invention must be measured ("stress gene mRNA"). This requires that total RNA or mRNA be isolated from exposed cells. This may be achieved by any of the numerous and well-known methodologies. Commercially available mRNA or total RNA isolation kits may also be utilized, such as is available from Strategene [La Jolla, Calif.]. Preferably the cells are lysed with guanidinium isothiocyanate (GTC). The lysate is then acidified with sodium acetate buffer (pH 5.2) and the contaminants extracted with phenol. The RNA is then twice precipitated with ethanol, dried and redissolved in water.

Once the RNA has been isolated, the level of stress gene mRNA can be measured in a number of ways, either directly or indirectly. In the direct method, oligonucleotides that are complementary to stress gene mRNA are used. In this method, the mRNA isolated from the cells is applied to nitrocellulose paper or nylon membrane filter in a slot blot apparatus. After diluting the RNA in the apparatus with appropriate salt solution (preferably two volume of 20X SSC) and washing the slots, the nitrocellulose paper or filter is either baked at 80° C. for 2 hours in a vacuum oven or UV crosslinked to fix the RNA. The RNA fixed to the nitrocellulose is then hybridized to labeled oligonucleotide probes which are complementary to stress gene mRNAs under appropriate buffer and temperature conditions.

An indirect method utilizes oligonucleotides that are homologous to stress gene mRNAs for detection. This method measures transcription by using the stress gene mRNAs as templates for making labelled single stranded cDNA using reverse transcription. These cDNAs are then detected and quantitated by hybridizing to complementary oligonucleotides (or denatured double-stranded cDNAs) that are bound to a solid support. Preferably, the solid support is a negatively charged membrane and the oligonucleotides are modified by the addition of a positively charged amidite or amino group on the 3' end prior to binding to the membrane. This 3' modification allows the oligonucleotide to bind to the membrane only via its 3' end, allowing for more efficient hybridization than other methods of binding DNA to a solid support.

In either method, a control representing a constitutively expressed "housekeeping gene", such as β-globin, β-tubulin, β-actin or γ-actin, which is not induced by the specific experimental sample, is also used. This provides a control for proper growth and functioning of the cells, as well as the background standard upon which to calculate the amount of specific induction. Following hybridization, the amount of hybridization is quantified. Quantification is achieved by a method that is consistent with the label on the oligonucleotide or cDNA. If a radioisotope is used as a label, exposure of the membrane to X-ray film followed by densitometry tracing or liquid scintillation counting would be the preferred methods of quantification. If a fluorescent label is used, a fluorometer is used for quantification. In this manner the level of various stress gene inductions can be measured. If a biotinylated label is used, quantification is achieved by using streptavidin conjugated to an enzyme that can yield a measurable calorimetric product.

It is known that while individual compounds may not be toxic, combinations of non-toxic compounds may in fact be toxic. Therefore, it should be understood that the kits and methods of this invention can also be utilized to determine the potential toxicity of combinations of known and unknown compounds (eg. drug interactions) in an identical manner to that described above.

This invention also provides stress-specific diagnostic kits and methods. For example, the invention provides redox stress kits and methods; DNA stress kits and methods; protein stress kits and methods; energy or ionic stress kits and methods; and receptor-mediated stress kits and methods. The choice of promoters to use in these stress-specific kits may be made from any of the appropriate promoters described or listed in Tables 1 and 2, above. Preferably these kits employ at least 3, and more preferably at least 8, promoters which respond to different subsets of stresses within the larger group. Most preferably, these specific kits and methods employ at least 12 promoters in those tables which respond to the appropriate stress. These kits and methods allow a more precise and specific analysis of the stresses caused by a compound.

According to another embodiment, the invention provides a method of identifying an antitoxin to a compound determined to be toxic by the methods of this invention. As described above, once a stress promoter induction profile is generated for an unknown compound, that profile is compared to profiles of known compounds in a database. A potential antitoxin to the unknown compound is a known antidote to a compound having a similar stress promoter induction profile.

In order to test the efficacy of such an antitoxin, the stress promoter assay is repeated using only those hosts containing stress promoters which were induced by the unknown compound. Each of those hosts is pre-incubated with varying concentrations of the proposed antitoxin prior to the addition of an inducing concentration of unknown compound. If pre-incubation with the proposed antitoxin decreases or obliterates the effect of the unknown compound, such an antitoxin will likely be effective.

Finally, this invention provides a method of improving active drug design. According to this embodiment, a new drug is first tested with any of the above-described kits and methods and its toxicity is determined. The information provided by such methods and kits indicates the cellular mechanism of the drug's toxicity. The portion of the drug that is likely to cause the particular cellular damage indicated may then be appropriately modified or eliminated depending upon the role that portion plays in the drug's pharmaceutical activity. The resulting modified drug is then retested with the kits and methods of this invention to determine if its toxicity has been sufficiently reduced or eliminated. Drugs improved and modified by this method are also within the scope of this invention.

In order that the invention described herein may be more fully understood, the following examples are set forth. It should be understood that these examples are for illustrative purposes only and are not to be construed as limiting this invention in any manner.

Certain of the basic molecular biology techniques described below are not set forth in detail. Such techniques are well known in the art and are described in the disclosure of *Molecular Cloning—A Laboratory Manual Second Edition*, J. Sambrook et al., eds., Cold Spring Harbor Laboratory Press, New York (1989), the disclosure of which is herein incorporated by reference.

EXAMPLE 1

Design And Synthesis Of Stress Gene-Specific Oligonucleotide Probes

The nucleotide sequence of each of the stress genes described herein is known. Accordingly, design of specific oligonucleotides is simply a matter of choosing what portion of the gene to model upon. The computer program OLIGO allows one to enter the nucleotide sequence of the gene of interest and analyze the sequence to determine position, length, and composition of oligonucleotides which will hybridize to the sequence of interest at salt concentrations and temperatures selected by the user. Using this program, I have designed the following stress gene-specific complementary oligonucleotides for use in the kits and methods of this invention:

GADD 153 gene: 5'-AAAAAAACCCAGTCCAACTA CAGA-CATGGCAGCTGAGTCCCTGCCATTCAC-CTTGGAGACGGTGTTTTTT-3';  [SEQ ID NO. 1]

XHF1 gene: 5'-AAAAAAGGCCAGTATGCACAGC TTTCCTC-CACTGCTGCTGCTGCTGTTCTGGGGT-GTGGTGTCTTTTTT-3';  [SEQ ID NO. 2]

JUN gene: 5'-AAAAAACCCCAAGATCCT GAAACAGAGCAT-GACCCTGAACCTGGCCGACCCAGTTTTTT-3';  [SEQ ID NO. 3]

MnSOD gene: 5'-AAAAAACAACCTGAAC GTCAACGAG-GAGAAGTACCAGGAGGCGTTGGCCAAGG-GAGATTTTTT-3';  [SEQ ID NO. 4]

HMO gene : 5'-AAAAAATAGAGCGTCCGCA ACCCGACAG-CATGCCCCAGGATTTGTCAGAGGCCCTTTTTT-3';  [SEQ ID NO. 5]

GST Ya gene: 5'-AAAAAAGGAGTTGGGAGCTG AGTG-GAGAAGAAGCCACGACTCTCGCTAGGT-CAGTACTCTTTTTT-3';  [SEQ ID NO. 6]

HSP70 gene: 5'-AAAAAAGCCGCGGCAGTCG GCATCGAC-CTGGGCACCACCTACTCCT-GCGTGGGGGTGTTCCAATTTTTT-3';  [SEQ ID NO. 7]

MDR-1 gene: 5'-AAAAAAATTACAGCAAGCC TGGAACCTAT-AGCCCCTTTAACTTGAGCAGCATCATTTTTTTT-3'  [SEQ ID NO. 8]

CYP 1A1 gene: 5'-AAAAAACATTCAGGGAAGG GTTGGG-TAGGTAGCGAAGAATAGGGATGAAGTCAGCTTTTTTT-3'  [SEQ ID NO. 9]

FOS gene: 5'-AAAAAATGCTGGAGAAGG AGTCTGCGGGT-GAGTGGTAGTAAGAGAGGCTATCCCCTTTTTT-3'  [SEQ ID NO. 10]

NMO1 gene: 5'-AAAAGGAATCTCATTTT
CTAGCTTTGATCTGGTTGTCAGTTGG-
GATGGACTTGCTTTTTT-3' [SEQ ID NO. 11]

ALDH2 gene: 5'-AAAAAACCTCTTGCTTCCC CGTGTTGATG-
TAGCCGAGGATCTTCTTAAACTGAGTTTTTTTT-3'
[SEQ ID NO. 12]

DRA gene: 5'-AAAAAACAGTGGTCAATGTCA CGTGGCTTC-
GAAATGGAAAACCTGTCACCACAGGATTTTTT-3'
[SEQ ID NO. 13]

MGMT gene: 5'-AAAAAAGGATTGTGAAATG AAACGCAC-
CACACTGGACAGCCCGTTGGGGAAGCTG-
GAGCTGTCTTTTTT-3' [SEQ ID NO. 14]

2'-5' AS gene: 5'-AAAAAATTCTTACAATTTT GGTACCAGT-
GCTTGACTAGGCGGATGAGGCTCTTGAGTTTTTT-3'
[SEQ ID NO. 15]

DHFR gene: 5'-AAAAAAAGTCTTGCATGATCCTT GTCA-
CAAATAGTTTAAGATGGCCTGGGTGATTCTTTTTT-3'
[SEQ ID NO. 16]

Cu.ZnSOD gene: 5'-AAAAAACCAGCACCCCGTCT CCGC-
GACTACTTTATAGGCCAGACCTTTTTT-3'
[SEQ ID NO. 17]

ALDHA1 gene: 5'-AAAAAAACCGTACTCTCC CAGTTCTCT-
TCCATTTCCAGACATCTTGAATCCACCATTTTTT-3'
[SEQ ID NO. 18]

TK gene: 5'-AAAAAAGAGTGTCTTTGGC ATACTTGATCAC-
CAGGCACTTGTACTGAGCAATCTGGTTTTTT-3'
[SEQ ID NO. 19]

PVALB gene: 5'-AAAAAAAAACACCTTCTTC ACATCATCCG-
CACTCTTTTTCTTCAGGCCGACCATTTTTTTT-3'
[SEQ ID NO. 20]

TH gene: 5'-AAAAAGAAGCTCTCAGACAC GAAGTAGACT-
GACTGGTACGTCTGGTCTTGGTAGGTTTTTT-3'
[SEQ ID NO. 21]

EH gene: 5'-AAAAATCTAGAATATAGG CAGCCAGACCCA-
CAGGAGAGTCATTCAGAGCAGAGCCTTTTTT-3'
[SEQ ID NO. 22]

TOP1 gene: 5'-AAAAAAGATAGCGCTCTTCTTC CCAC-
CATTTCCACTTCTGTTCCTCTTCTTTCTTCTTTTTT-3'
[SEQ ID NO. 23]

TOP2 gene: 5'-AAAAAGCCTCTGCCAGTTTTTCTT CAGT-
CATCTTCACAACAAATTTCACAGTGGTTTTTTT-3'
[SEQ ID NO. 24]

MT 1A gene: 5'-AAAAAATCTCTTCCTTGCAG GTGGCTCCT-
GCACCTGCACTGGCTCCTGCAAATG-
CAAAGAGTTTTTT-3' [SEQ ID NO. 25]

The synthesis of the above oligonucleotides was carried out as follows. The specific oligonucleotide was synthesized using an automated oligonucleotide synthesizer [Model 392, Applied Biosystems, Foster City, Calif.].

I have also designed the following oligonucleotides which are homologous to the indicated stress gene mRNAs, based on the reported nucleotide sequence of the various genes or cDNAs thereof:

ALDH1 gene: 5'-AATTGCTATGGCGTGGTAAGTG CCCAGT-
GCCCCTTTGGTGGATTCAAGAT-3' [SEQ ID NO. 26]

CYP1A1 gene: 5'-ATCTGAGTTCCTACCTGAACGGT TTCT-
CACCCCTGATGGTGCTATCGACA-3' [SEQ ID NO. 27]

FOS gene: 5'-GTACTCCCAGCTGCACTGCT TACACGTCTTC-
CTTCGTCTTCACCT-3' [SEQ ID NO. 28]

GADD153 gene: 5'-AGGAGAATGAAAGGAAAGTGGC
ACAGCTAGCTGAAGAGAATGAACGGCTC-3'
[SEQ ID NO. 29]

GADD45 gene: 5'-AGTCGCTACATGGATCAATGGGT
TCCAGTGATTAATCTCCCTGAACGGTG-3'
[SEQ ID NO. 30]

GAPDH gene: 5'-GTGGTGGACCTGACCTGCCGTCT
AGAAAAACCTGCCAAATATGATGACAT-3'
[SEQ ID NO. 31]

GST2 gene: 5'-CAGCCCAAGGAAGCCTCCCATGG
ATGAGAAATCTTTAGAAGAAGCAAGGA-3'
[SEQ ID NO. 32]

HMO gene: 5'-CTTACACTCAGCTTTCTGGTGGCG ACAGT-
TGCTGTAGGGCTTTA-3' [SEQ ID NO. 33]

HSP70 gene: 5'-AGAAGGACGAGTTTGAGCACAAG
AGGAAGGAGCTGGAGCAGGTGT-3' [SEQ ID NO. 34]

JUN gene: 5'-GCTCAGGGAACAGGTGGCACAGC TTAAACA-
GAAAGTCATGAACCACGTTA-3' [SEQ ID NO. 35]

MDR1 gene: 5'-GAAAGGCATCTATTTTTCAATGGT CAGT-
GTCCAGGCTGGAACAAAGCGCC-3' [SEQ ID NO. 36]

MT1A gene: 5'-GCACTGGCTCCTGCAAATGCAAA GAGTG-
CAAATGCAACTCCTGCAAG-3' [SEQ ID NO. 37]

MTIIA gene: 5'-CCCAGGGCTGCATCTGCAAAG GGGCGTCG-
GACAAG-3' [SEQ ID NO. 38]

NMO gene: 5'-ACCACTGTATTTTGCTCCAAGCAGC
CTCTTTGACCTAAACTTCCAGGCAG-3' [SEQ ID NO. 39]

PCNA gene: 5'-ACAAAAGCCACTCCACTCTCTTCA ACGGT-
GACACTCAGTATGTCTGCAGA-3' [SEQ ID NO. 40]

NQO gene: 5'-TTGCTCTCGACAGTATCCACAAT AGCTGACG-
GCTGGGTGTTTCAGTTTGA-3' [SEQ ID NO. 41]

I also designed the following control oligonucleotides which are homologous to housekeeping gene transcripts:

ACTG (gamma-actin) gene: 5'-ACCTTCCAGCA GATGTGGATT-
AGCAAGCAGGAGTACGACGAGTCG-3' [SEQ ID NO. 42]

BTUB (beta-tubulin) gene: 5'-TTGAGTGG ATCCCCAACAAT-
GTGAAAACGGCTGTCTGTGACATCCCACCT-3'
[SEQ ID NO. 43].

These oligonucleotides were each modified at their 3' end by the addition of an amino group so that they could bind to a negatively charged membrane only via their 3' end. Such oligonucleotides were synthesized to order by Operon Technologies, Inc., Alameda, Calif.

Complementary and homologous oligonucleotide probes for any of the other stress gene mRNAs that may be employed in this invention may be similarly designed using the software described above.

EXAMPLE 2

Toxicity Assay of an Unknown Compound Using Radiolabelled Oligonucleotide Probes I. Direct Quantification of Stress Gene mRNA by Hybridization to Oligonucleotide Probes It is desirable to know if unknown compound "X" is toxic and, if it is, what type of damage it causes to mammalian cells.

HepG2 cells are grown in 165 cm² flasks containing minimal essential medium (Gibco/BRL, Gaithersburg, Md.) until they reach a density of approximately $8 \times 10^6$ cells/ml. The cells are then subcultured by diluting them to $5 \times 10^6$ cells/ml and plated at 10 ml/plate. Several plates of each subculture are exposed to a different concentration of compound X (1 pM to 1 mM in a series of 10-fold dilutions). Messenger RNA is isolated from subcultures after 2, 4, 8, 16 and 32 hours, as described below.

The medium is removed from the cell monolayers by aspiration and the cells are washed twice with cold phosphate buffered saline. I then add 2 ml of cold phosphate buffered saline to the monolayer and use a rubber policeman to scrape the lysate into 15 ml disposable polypropylene tubes. Total RNA was isolated using the RNAzol B reagent (Biotecx Laboratories, Houston, Tex.), following manufacturer's directions. The RNA pellet is dried and redissolved in 10 µl water. A normal yield of RNA is about 100–200 µg/plate.

RNA from each two replicate plates is then applied to 20 different slots in a slot blot apparatus as follows. The slot blot apparatus is cleaned prior to use in 0.1N NaOH. A piece of nitrocellulose paper or nylon membrane filter (0.45 µm pore size) is briefly wetted in water and then soaked in 20X SSC for 1 hour at room temperature. The filter is then placed in the apparatus. The RNA sample from each plate is mixed with 20 µl of 100% formamide, 7 µl of 37% formaldehyde and 2 µl of 20X SSC, incubated at 68° C. for 15 minutes and then chilled on ice.

Twenty µg of RNA is applied to each slot in the apparatus together with two volumes of 20X SSC. After the solution drains through the filter, the slots are rinsed twice with 1 ml of 10 X SSC. The filter is then dried and baked at 80° C. for 2 hours in a vacuum oven. The filter is then cut into strips so that samples exposed to different concentrations of X for varying periods of time can be hybridized to individual stress gene-specific probes. One strip is used for each separate probe.

Hybridization of the strips to individual oligonucleotide probes are carried out under well known conditions for RNA-DNA hybridization. The temperature and salt concentration for hybridizing various probes to the RNA will depend upon the nature of the oligonucleotide. These conditions can be calculated using well known formulae. Probes to the following genes are used:

redox stress only: CYP1A1, NMO1, ALDH2;

DNA stress only: XHF, DRA, GADD153 and MDR-1; protein stress only: HSP70, MT 1A; redox and DNA stress: GST Ya, HMO and MnSOD; redox, DNA and protein stress: JUN; DNA, protein and energy/ionic stress: FOS.

Following hybridization, the strips are washed, dried and mRNA levels are quantified in one of two ways. In one method, the strips are exposed to X-ray film and hybridization is quantified by densitometry. Alternatively the strips are put into individual slots and subjected to scintillation counting. Actually, both methods can be carried out if the former is performed first.

II. Indirect Quantification of Stress Gene mRNA by Hybridization of cDNA to Oligonucleotide Probes A. Cross-Linking of Oligonucleotides to Negatively Charged Membrane We separately cross-linked oligonucleotides homologous to the mRNAs of the following stress and housekeeping genes to Biodyne C membranes (Pall Corporation, East Hills, N.Y.) essentially using the method described in Y. Zhand et al., *Nucleic Acids Res.*, 19, pp. 3929–33 (1991):

redox stress only: CYP1A1, ALDH1; DNA stress only: GADD153; protein stress only: HSP70; redox and protein stress: MTIIA; redox and DNA stress: HMO; redox, DNA and protein stress: JUN; DNA, protein and energy/ionic stress: FOS; control: γ-actin.

The Biodyne C membrane was first rinsed briefly with 0.1N HCl. We then treated the membrane for 15 minutes with freshly prepared 20% (w/v) EDC (1-ethyl-3-(3-dimethylaminopropylcarbodiimide)). The membrane was then rinsed with H₂O and placed on a 96-well Dot-Blot apparatus. We then applied the amino-modified oligonucleotides in 0.5M NaHCO₃ (pH 8.4) to the membrane in individual wells using a vacuum for 15 min. The total volume per well should not exceed 3 µl. Each individual oligonucleotides was applied in four adjacent wells.

After applying the oligonucleotides, we rinsed the membrane with 1×TBS/0.1% TWEEN-20™ and then quenched any remaining active groups on the membrane by treating with 0.1N NaOH for 10 min. We then rinsed the membrane with dH₂O, air dried, and stored the dry membrane in a sealed plastic bag.

B. Treatment of Cells and Isolation of RNA

HepG2 cells are grown in minimal essential medium in 100 mm cell culture dishes to no greater than 80% confluency. The cultures are then exposed to various concentrations of compound X and are incubated at 37° C. for the desired length of time. After aspirating off the media, the cells are washed three times with 10 ml of a room temperature phosphate buffered saline solution. 5 ml of the phosphate buffered saline solution is then added to the cell culture dish and the cells are scraped from the dish with a rubber policeman and placed in a 15 ml centrifuge tube. Cells are the counted with a hemacytometer and pelleted in a centrifuge. The phosphate buffered saline is poured off.

If total RNA isolation is desired, we use RNAzol B (Biotecx Laboratories, Inc., Houston, Tex.), following manufacturer's directions. If only mRNA is desired, the Messenger RNA Isolation Kit (Stratagene Inc., La Jolla, Calif.) is used, following the manufacturer's directions.

3. Reverse Transcription and Optional PCR of Stress-Specific cDNAs

Total RNA (50 µg) or mRNA (2 µg) isolated by the procedures described above is then reverse transcribed using SUPERSCRIPT II (reverse transcriptase) (Gibco/BRL, Gaithersburg, Md.) and the following protocol.

The RNA is added to a microcentrifuge tube with DEPC H₂O and oligo-dT primer. The amount of DEPC H₂O added to the reaction mix is determined after the volumes of the other reagents are determined. The oligo-dT primer (0.5 µg/µl) is added so that the volume is 10% of the total end volume. The reaction mixture is heated to 70° C. for 10 min and then quick-chilled on ice. The following components are added in the order: 5x SUPERSCRIPT first strand buffer (20% of total volume); 0.1M DTT (10% of total volume); 10 mM dNTP mix (5% of total volume); SUPERSCRIPT II™ (5% of total volume). The reaction mixture is centrifuged briefly and then mixed by repeated pipetting. The mixture is incubated at 37° C. for 1 hour. 2 µl of RNAse A (10 mg/ml) is then added to the reaction mixture and mixed by pipetting. The reaction mixture is then incubated at 37° C. for another hour. At the end of incubation, ddH₂O is added to a final volume of 450 µl. The cDNA is precipitated by adding 50 µl of 3M sodium acetate, followed by 1 ml of 100% ethanol. The mixture is then centrifuged for 30 minutes in a microcentrifuge at 12,000×g. The supernatant is removed and the cDNA resuspended in 100 µl of ddH₂O. 2 µl of the resuspended cDNA is then removed and read in a scintillation counter. A total of 1,000,000 cpms is required for hybridization.

The cDNA may be either radiolabelled through the use of α-$^{32}$P dCTP (100 μCi) in the reaction or chemically labelled through the use of digoxigenin-dUTP using the GENIUS 1™ kit (Boehringer Mannheim Biochemical, Indianapolis, Ind.).

If an insufficient quantity of stress gene cDNA is obtained by the above process, PCR may be used for amplification. Reverse transcription is carried out as described above, except that no label is incorporated into the cDNA. Primers based on the published 5' and 3' coding sequences of the desired stress gene are used in the PCR reaction. Amplification of all stress gene cDNAs is carried out in the same reaction tube.

The total cDNA is diluted 1:10 with dH$_2$O and 10 μl is used for the PCR reaction. The following components are then added to produce the indicated final concentration: 1x TAQ buffer (Boehringer Mannheim Biochemical); 300 μM each dNTP; 25 pmol each PCR primer; 2.5 units TAQ polymerase (Boehringer Mannheim Biochemical); dH$_2$O to a total reaction volume of 50 μl. The mixture is mixed by pipetting, followed by a 2 second centrifugation. Two drops of light mineral oil are placed on top of the reaction mixture. PCR is set then carried out for 30 cycles of 1 minute at 95° C.; 2 minutes at T$_m$+2° C.; 3 minutes at 72° C. (10 minutes during last cycle). The PCR products are labelled with $^{32}$P that has been incorporated into nested primers via a kinase reaction in a one-cycle PCR reaction.

A nested primer is a primer based on a stress specific nucleotide sequence located inside of the sequences upon which the primers for PCR were based. These primers are synthesized using an oligonucleotide synthesizer or purchased from a commercial contractor. The nested primers are labelled by mixing 1.2 μl (0.5 μg/μl) of nested primer with 1.0 μl of 10x kinase buffer (0.5M Tris, pH 8.2, 0.1M MgCl$_2$, 50 mM DTT); 5.0 μl α-$^{32}$P ATP; 1.0 μl polynucleotide kinase and 1.8 μl dH$_2$O. The reaction is mixed by pipetting and incubated at 37° C. for 1 hour. The reaction is terminated by incubation at 70° C. for 10 minutes, followed by a quick centrifugation and cooling on ice. 90 μl of dH$_2$O are then added, followed by 100 μl of phenol/chloroform (1:1). The mixture is mixed well, centrifuged for 10 minutes, and the aqueous phase is then transferred to a new tube. We then precipitate the labelled primers by adding 10 μl of 3M sodium acetate, 1 μl of 10 mg/ml tRNA, and 400 μl of 100% ethanol and placing on ice for 10 minutes. The mixture is the centrifuged for 30 min at room temperature. The pellet is washed with 80% ethanol, centrifuged for 5 seconds and dried. The pellet is resuspended with 4 μl dH$_2$O, 0.5 μl 10x TAQ buffer, and 0.5 μl TAQ enzyme.

We then add 5 μl of the labeled nested primers to the aqueous phase of the above-described PCR mixture under the mineral oil and perform an additional cycle of PCR by heating to 95° C. for 2 minutes, cooling to T$_m$+2° C. (of labeled primer) for 2 minutes and warming to 72° C. for 10 minutes.

We then remove 50 μl of the aqueous phase to a new tube, add 50 μl dH$_2$O, 100 μl phenol/chloroform, mix well, and centrifuge for 10 minutes. The aqueous phase is recovered into a fresh tube. Unincorporated primers are removed using a spin column.

4. Hybridization

The membrane containing the cross-linked oligonucleotides is wetted in 15 ml of RAPID HYB buffer (Amersham, Arlington Heights, Ill.) by holding one end of the membrane with a pair of tweezers and slowly immersing the membrane. The membrane is then prehybridized by transferring to a Seal-a-Meal bag, the 15 ml of RAPID HYB buffer from the wetting step is added, and the bag is sealed. It is then immersed in a 68° C. shaking water bath for 1 hour. The labelled cDNA (15,000,000 cpms) is diluted into 1 ml of RAPID HYB™ and boiled for 10 minutes followed by quick-chilling on ice.

After prehybridization, the RAPID HYB™ is removed and replaced with 14 ml of fresh RAPID HYB™ preheated to 65° C. The labelled cDNA is then added to the bag and the end is resealed. The bag is then immersed in a 68° C. shaking water bath overnight. After hybridization, the membrane is removed from the bag and placed into a tray containing low stringency buffer (2x SSC/0.1% SDS) for 20 minutes at room temperature. The membrane is then transferred to high stringency buffer (0.2x SSC/0.1% SDS; preheated to 45° C.), and shaken for 30 minutes at 45° C. The membrane is then removed from the high stringency wash, placed on a piece of Whatman 3MM® filter and exposed to X-ray film at −70° C. overnight with an intensifying screen. After development, the autoradiograph is cut to fit into a 96-well microtiter plate holder and taped such that the radioactive dots are aligned with the holes in the holder. The autoradiograph is then read at 600 nm for quantification.

The results for either of the two above-described assays are then compared to a database of standards prepared using the above promoters and known toxins. By correlating results for X with known compounds, a toxicity profile can be created. For example, if X induced the same stress genes as TCDD at similar concentrations, this would indicated that X is toxic to whole animals at similar concentrations as TCDD.

EXAMPLE 3

Construction of Stress Promoter-CAT Fusions

I prepared an XHF promoter-CAT fusion as follows. I synthesized two oligonucleotides based upon the published sequence of the XHF (collagenase) promoter [P. Angel et al., *Mol. Cell Biol.*, 7, pp. 2256–66 (1987)]. One corresponded to positions −520 to −501 upstream from the transcription start site primer. [SEQ ID NO. 44]: 5'-TACCAGGCAGCT TAACAAAG-3'. The other corresponded to positions +53 to +73 downstream from the transcription start site. [SEQ ID NO. 45]: 5'-ACTGGCCTTTGTCTTCTTTC-3'. The oligonucleotides were synthesized by Operon Technologies (Alameda, Calif.). The oligonucleotides were dissolved in water at a final concentration of 500 pmoles/ml.

For XHF promoter amplification I mixed 0.1 μg of Raji (human genomic library) genomic DNA, 20 pmoles of each of the above two primers, 5 μl of 10X buffer [500 mM KCl, 100 mM Tris-HCl, pH 8.3, 15 mM MgCl$_2$, 0.1% gelatin], 5 μl of 2.0 mM of each dNTP and 1 unit of AMPLITAQ™ (Taq polymerase) (Perkin-Elmer, Norwalk, Conn.). I added water to a total volume of 50 μl and performed PCR.

The PCR reaction was run at 94° C. for 2 minutes, followed by 30 cycles of: 10 seconds at 56° C., 30 seconds at 71° C. and 10 seconds at 94° C. The PCR reaction was completed by incubating the mixture at 56° C. for 1.5 minutes followed by 71° C. for 4 minutes. The reaction product was then electrophoresed on a 1.0% agarose gel and the amplified sequence excised from the gel and purified. The isolated fragment was then kinased and blunt-end ligated into the pBLCAT3 vector described in B. Luckow et al., *Nucl. Acids Res.,* 15, p. 5490 (1987), the disclosure of which is herein incorporated by reference.

Other stress promoter-CAT fusions may be similarly prepared using any of the above-cited, published nucleotide sequences of the various stress gene promoter regions to design appropriate oligonucleotide primers for PCR. CAT fusions with the following stress promoters were prepared for use in the kits and methods of this invention: XHF, CYP1A1, GST Ya, MTIIA, FOS, HSP70, GADD45, GADD153 and JUN.

EXAMPLE 4

Construction of a Response Element-CAT Fusion

I constructed a xenobiotic response element XRE-CAT fusion as follows. I first had oligonucleotides corresponding to both strands of the XRE synthesized by an independent contractor (Operon Technologies, Inc., Alameda, Calif.). The sequence of the XRE is described in M. Denison et al., *J. Biol. Chem.,* 263, pp. 17221–24 (1988). The oligonucleotides were synthesized with overhanging BamHI compatible ends.

The oligonucleotides were dissolved in water at a final concentration of 500 pmoles/ml. I then mixed 50 μg of each oligonucleotide together in a solution containing 500 mM NaCl, 50 mM Tris-HCl, pH 7.8, 1 mM EDTA and boiled for 5 minutes. I then incubated the solution overnight at 68° C. to allow the strands to anneal to one another. The double stranded oligos were then electrophoresed on a 12% polyacrylamide gel and purified by excising the band and electroeluting the DNA.

The purified response elements were then kinased and cloned into the BamHI site of pBLCAT2 (M. Denison et al., *J. Biol. Chem.,* 263, pp. 17221–24 (1988)], just upstream of the tk minimal promoter.

Other response element-CAT fusions may be similarly prepared using any of the above-cited, published nucleotide sequences of the various response elements to design appropriate oligonucleotide primers for PCR. CAT fusions with the following response elements were prepared for use in the kits and methods of this invention: XRE, NFkB, CRE, p53RE and RARE.

EXAMPLE 5

Assay of Toxins Using Stress Promoter-CAT Fusions

Approximately $5 \times 10^4$ cells of each of the 14 transformed strains described in Examples 3 and 4 above were separately plated into a row of 12 wells in one of two 96-well plates. An untransformed human liver cell line was plated into the wells of the last row of the second plate to determine cell viability. The cells were grown in 10% Complete Minimal Essential Media (Gibco/BRL, Gaithersburg, Md.) at 37° C., 5% $CO_2$ until reaching 90% confluency.

We tested five or six different concentrations of the various chemicals listed in Table 3, below, dissolved in the appropriate solvent in triplicate.

TABLE 3

| Test Compounds | | |
|---|---|---|
| Compound | Solvent | Concentration Range |
| 3-MC | DMSO | 1 nM–10 μM |
| Sodium arsenate | water | 1 nM–10 μM |

TABLE 3-continued

| Test Compounds | | |
|---|---|---|
| Compound | Solvent | Concentration Range |
| DMSO | none | .001–10% (v/v) |
| Cadmium sulfate | water | 100 nM–10 μM |
| Benzo[a]pyrene | DMSO | 10 nM–100 μM |
| Ethanol | none | .001–10% (v/v) |
| PMA | ethanol | 3.2–200 ng/ml |
| MMS | water | 10 ng/ml–100 μg/ml |
| Methapyrilene | water | 10 nM–100 μM |
| TCDD | DMSO | 1 nM–10 μM |
| Retinoic acid | DMSO | 10 nM–100 μM |

The various concentrations were made by performing a dilution series. For TCDD, we first removed 20 μl of media from each well in columns 3 through 10 and 10 μl from columns 11 and 12 of the 96 well plates. We placed 10 μl of a 200 μM solution of test chemical into each well in columns 11 and 12. The liquid in those wells was mixed well with a multichannel pipetman using separate pipette tips for each row, and 20 μl was then transferred from the wells in column 12 to column 10. The liquid in column 10 was mixed and 20 μl then transferred to column 8 and the procedure repeated for the even numbered columns down to column 4. The same procedure was carried out for the odd numbered columns starting with column 11 and ending with column 3. Columns 1 and 2 of each row represent untreated controls. The plates were then incubated at 37° C., 5% $CO_2$ overnight.

At the end of the incubation the media was gently aspirated from all of the wells except the cell viability row on the second plate. The cells in all but that last row were washed twice with 200 μl of phosphate buffered saline. After the wash, we added 100 μl of Cell Lysis Buffer (5 mM Mops, 2.5 mM NaCl, 0.38 mM $MgCl_2$, 0.25% Triton X-100, pH to 6.5 using NaOH) to each well and incubated 30 minutes at room temperature. We then combined the lysates in the wells containing duplicate concentrations of chemical by transferring the 100 μl of lysate in column 12 to column 11, column 10 to column 9, and so on.

We assayed the total protein in each well as follows. In two fresh 96 well plates we added 190 μl of 1X Protein Assay Reagent (Bio-Rad Laboratories, Hercules, Calif.) to each well in column 1 through 7. We transferred 10 μl of cell lysate from the wells in column 1 of the toxin test plate to column 2 of the protein assay plate, from column 3 of the toxin test plate to column 3 of the protein assay plate, from column 5 of the toxin test plate to column 4 of the protein assay plate and so on. The plates were then incubated for 15 minutes at room temperature and then the absorbance of each well read at $OD_{600}$.

The CAT assay was performed using a CAT ELISA kit (5 Prime-3 Prime, Inc., Boulder, Colo.) and following the manufacturer's directions. We used 190 μl of each cell lysate in the toxin test plates for determining CAT activity. The CAT assay was allowed to proceed for three and one-half hours at room temperature. CAT activity was measured by using a biotinylated anti-CAT antibody, followed by a streptavidin conjugated alkaline phosphatase, and finally the calorimetric substrate, p-nitrophenyl-phosphate. Color development was measured at $OD_{405}$.

Fold-induction was calculated using the following formula:

$$\frac{OD_{405}(\text{test sample})/OD_{600}(\text{test sample})}{OD_{405}(\text{control})/OD_{600}(\text{control})}$$

Figure 2:
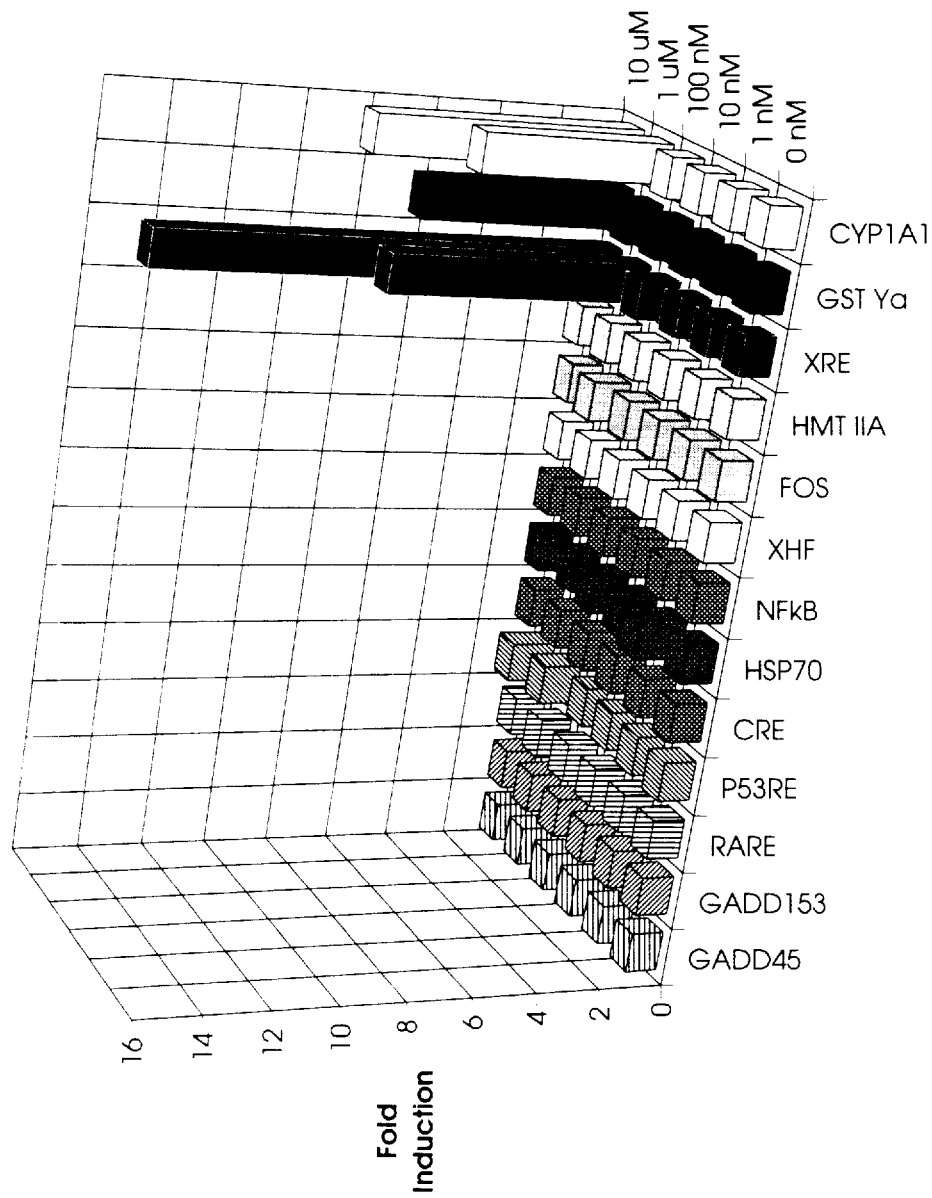
FIG. 2 depicts the relative expression of chloramphenicol acetyl transferase under the control of different stress promoters in the presence of varying concentrations of 3-methyl cholanthrene (3-MC).
Figure 3:
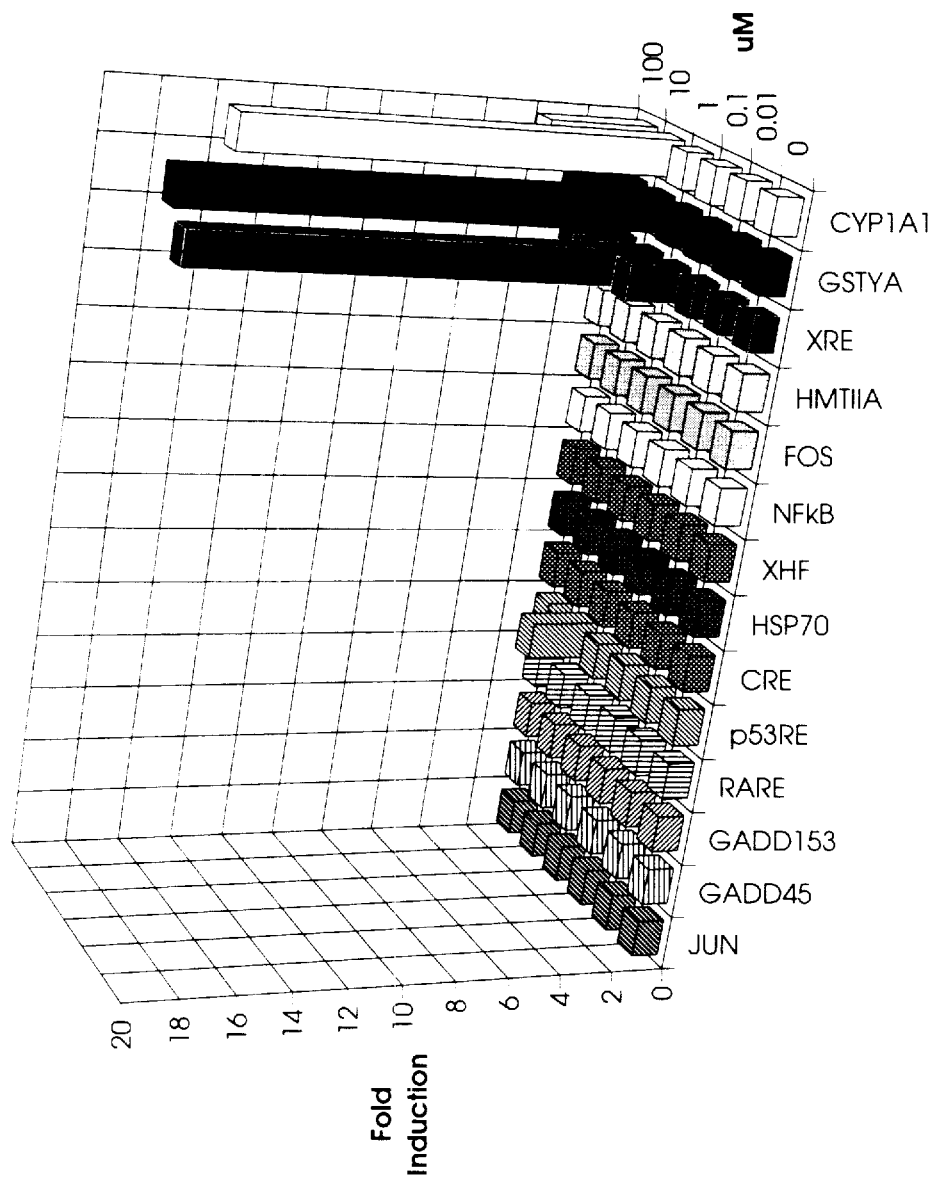
FIG. 3 depicts the relative expression of chloramphenicol acetyl transferase under the control of different stress promoters in the presence of varying concentrations of benzo [a]pyrene.
Figure 4:
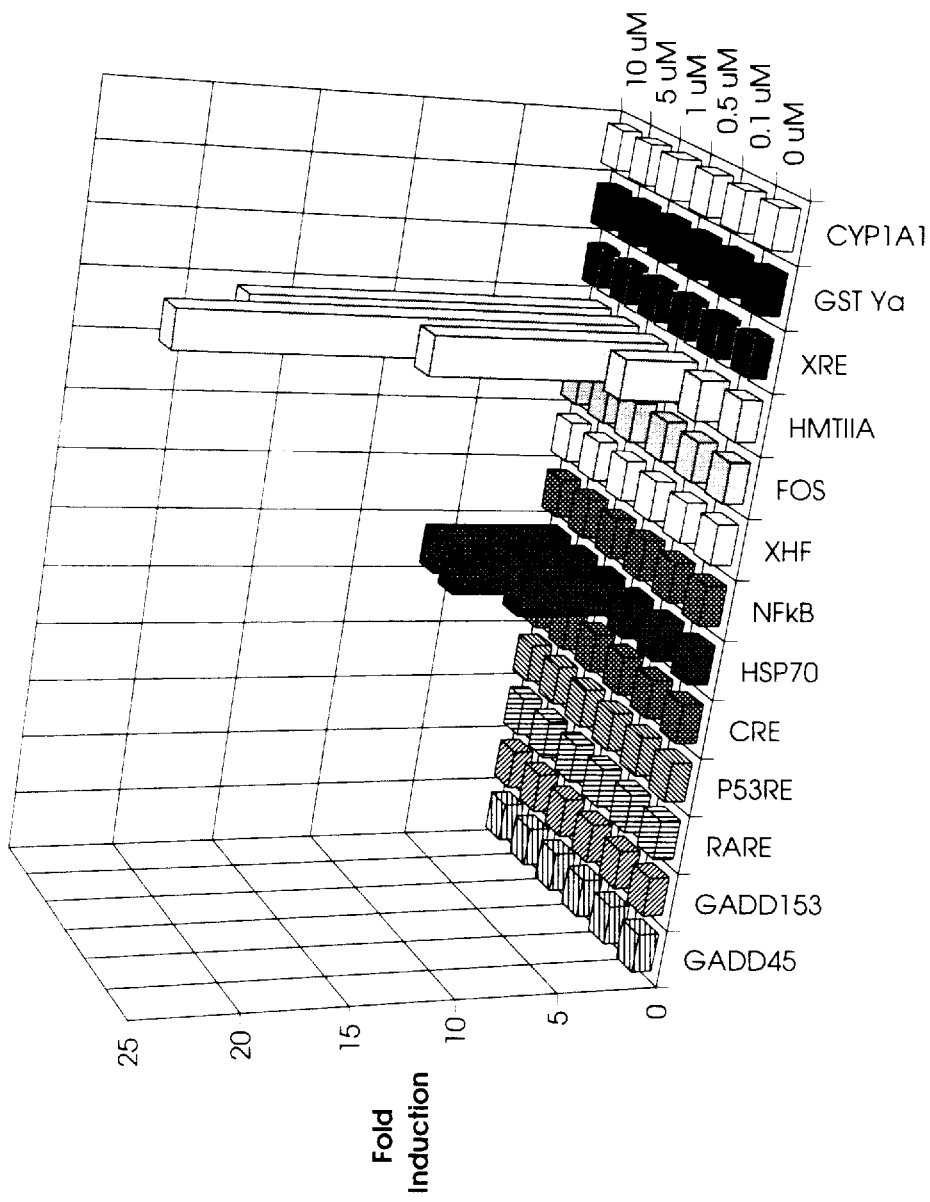
FIG. 4 depicts the relative expression of chloramphenicol acetyl transferase under the control of different stress promoters in the presence of varying concentrations of cadmium sulfate.
Figure 5:
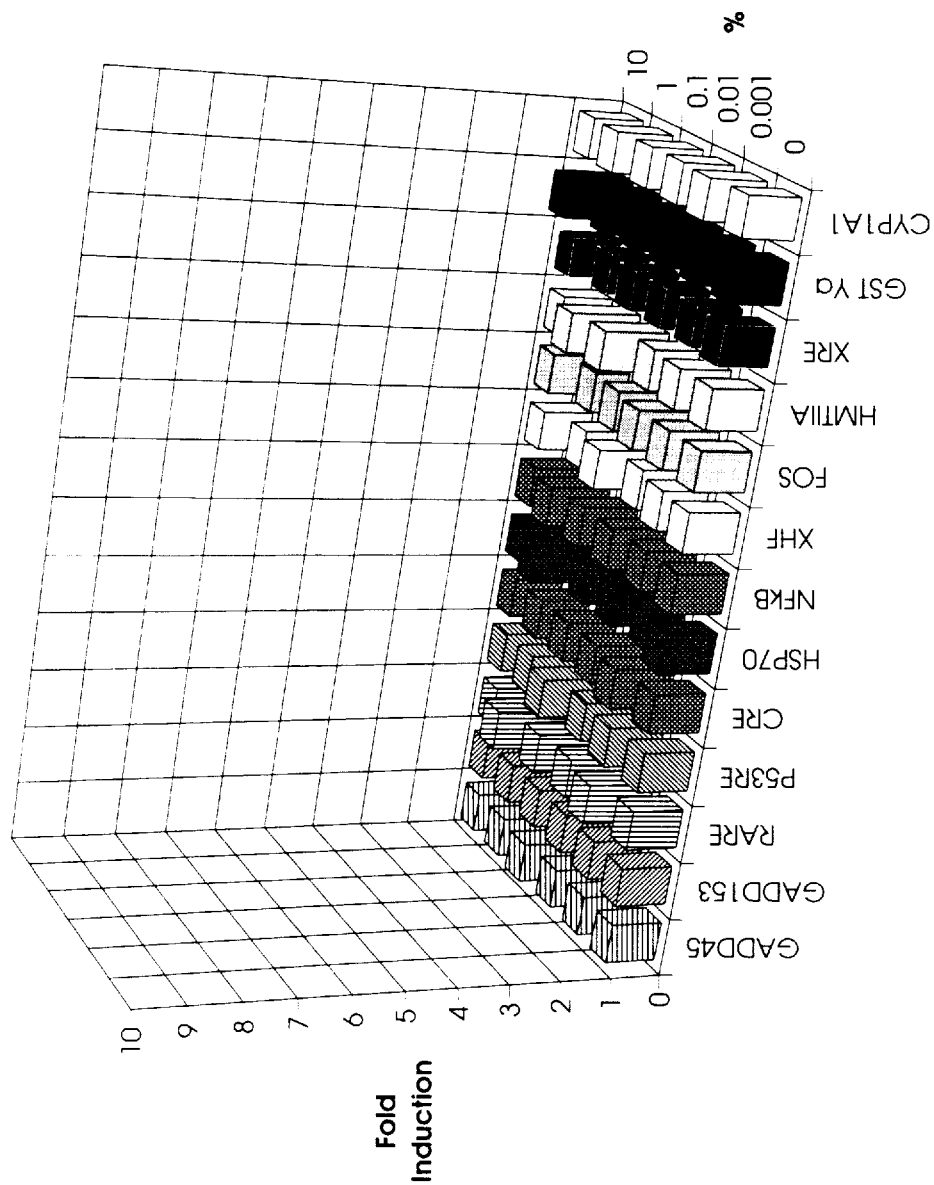
FIG. 5 depicts the relative expression of chloramphenicol acetyl transferase under the control of different stress promoters in the presence of varying concentrations of dimethyl sulfoxide (DMSO).
Figure 6:
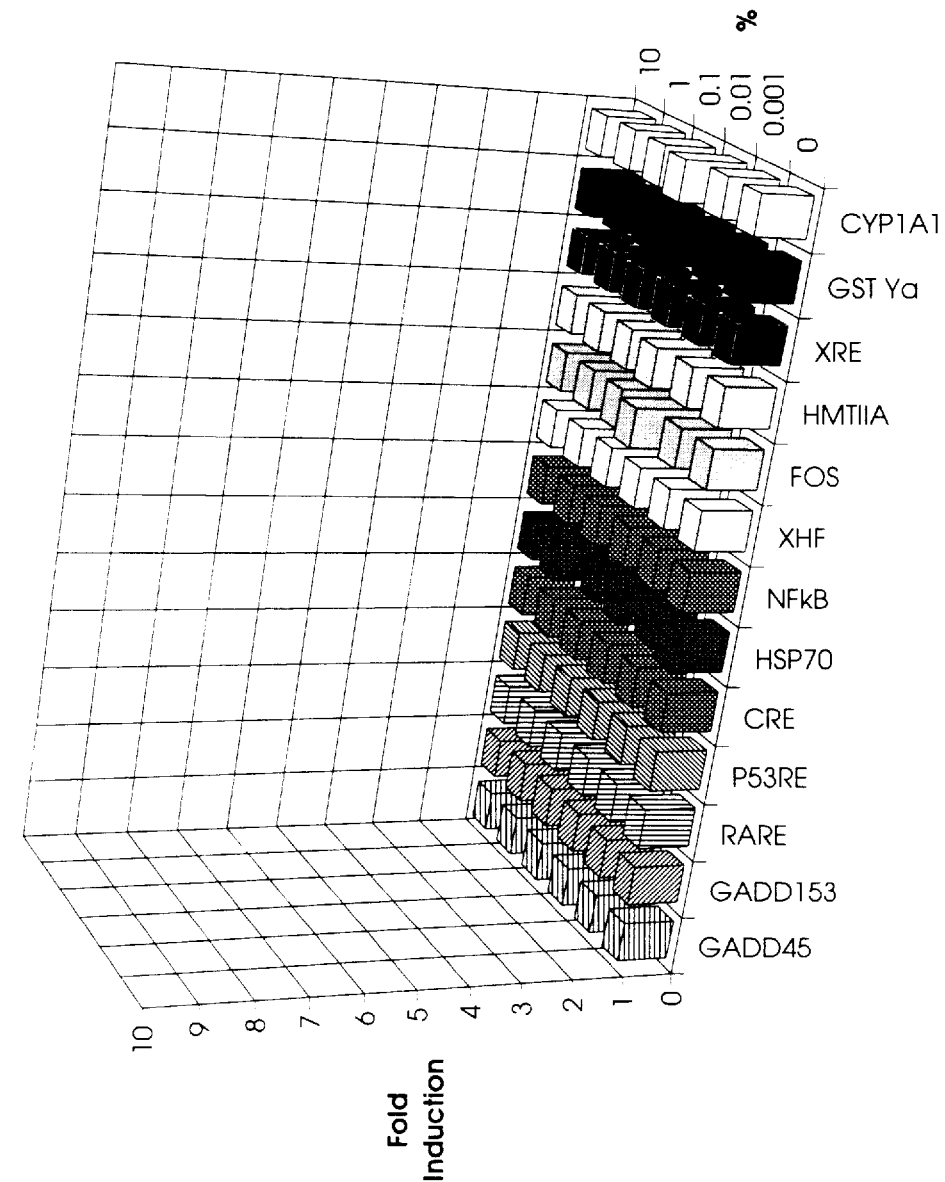
FIG. 6 depicts the relative expression of chloramphenicol acetyl transferase under the control of different stress promoters in the presence of varying concentrations of ethanol.
Figure 7:
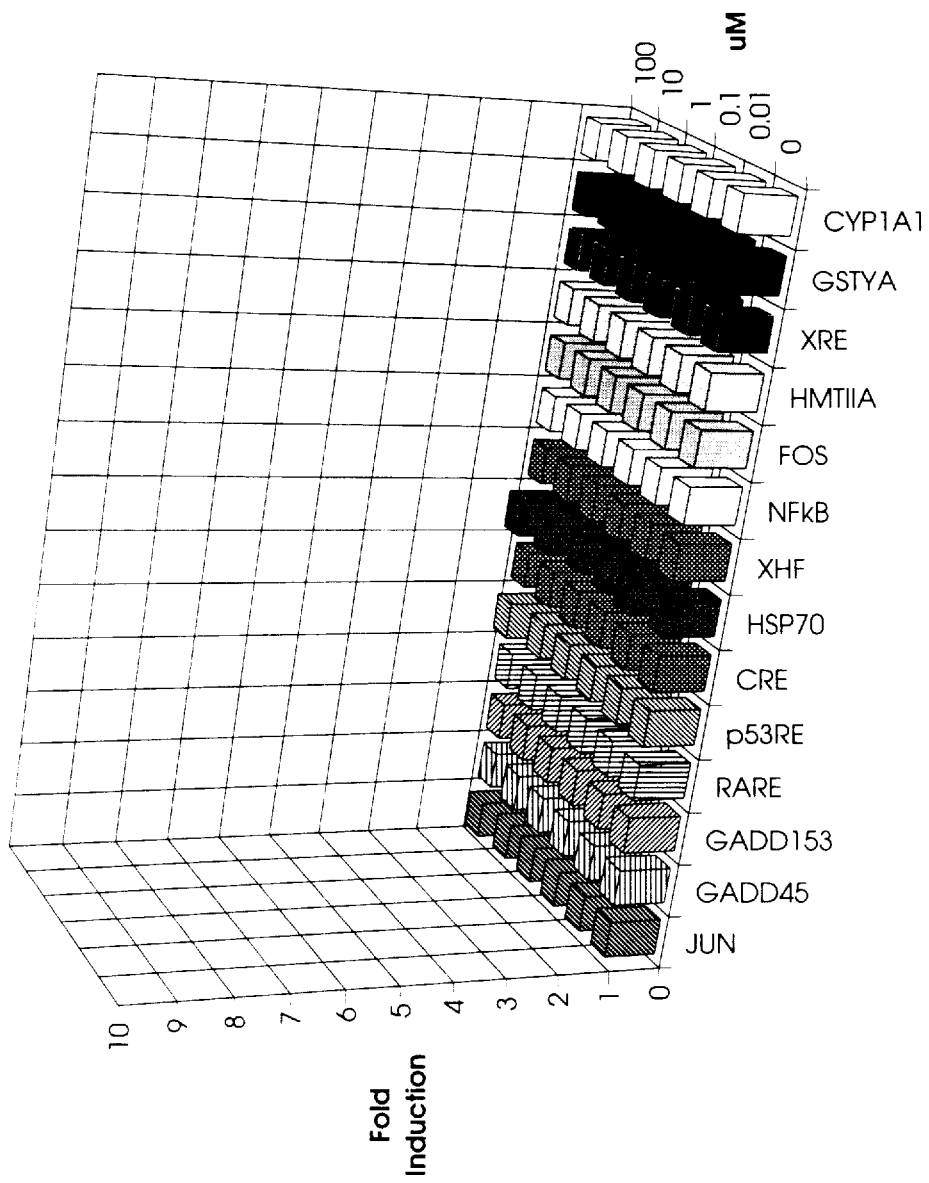
FIG. 7 depicts the relative expression of chloramphenicol acetyl transferase under the control of different stress promoters in the presence of varying concentrations of methapyrilene hydrochloride.
Figure 8:
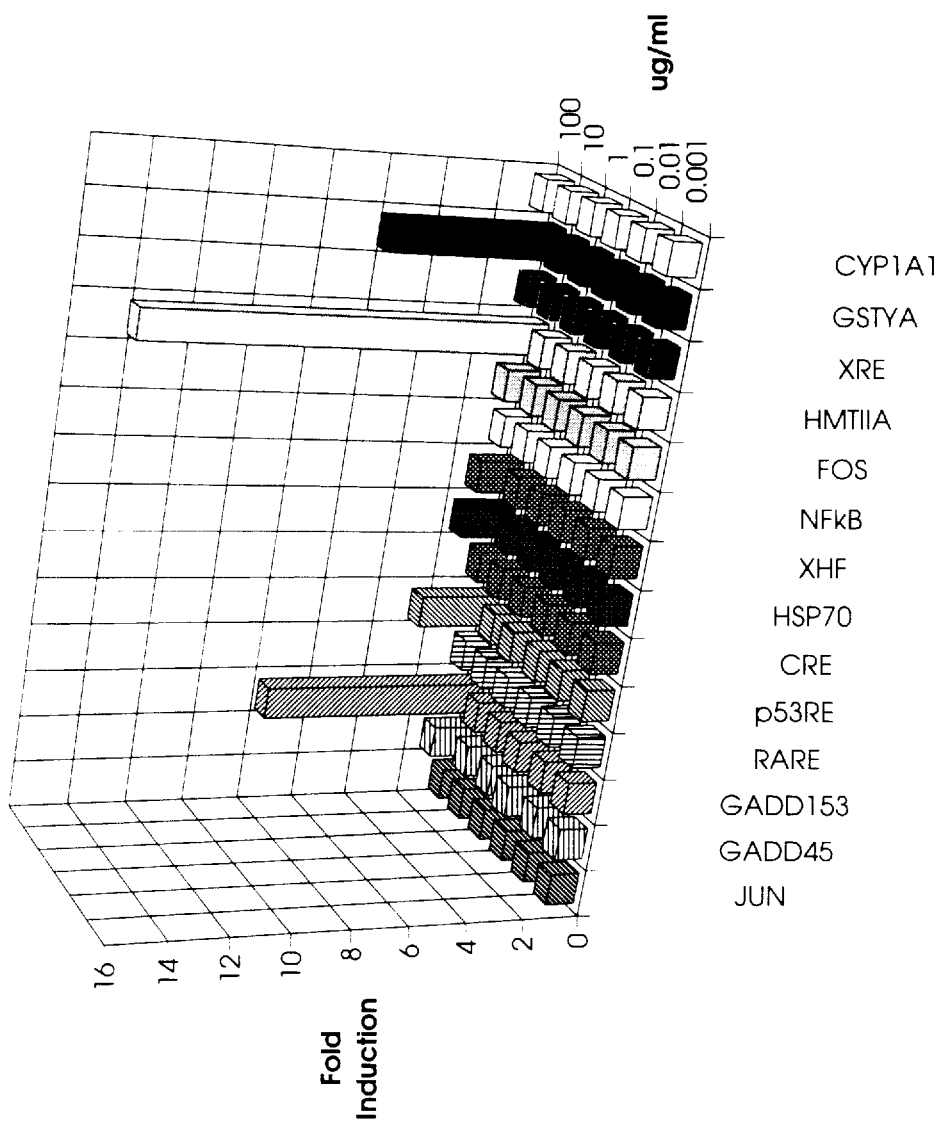
FIG. 8 depicts the relative expression of chloramphenicol acetyl transferase under the control of different stress promoters in the presence of varying concentrations of methyl methanesulfonic acid (MMS).
Figure 9:
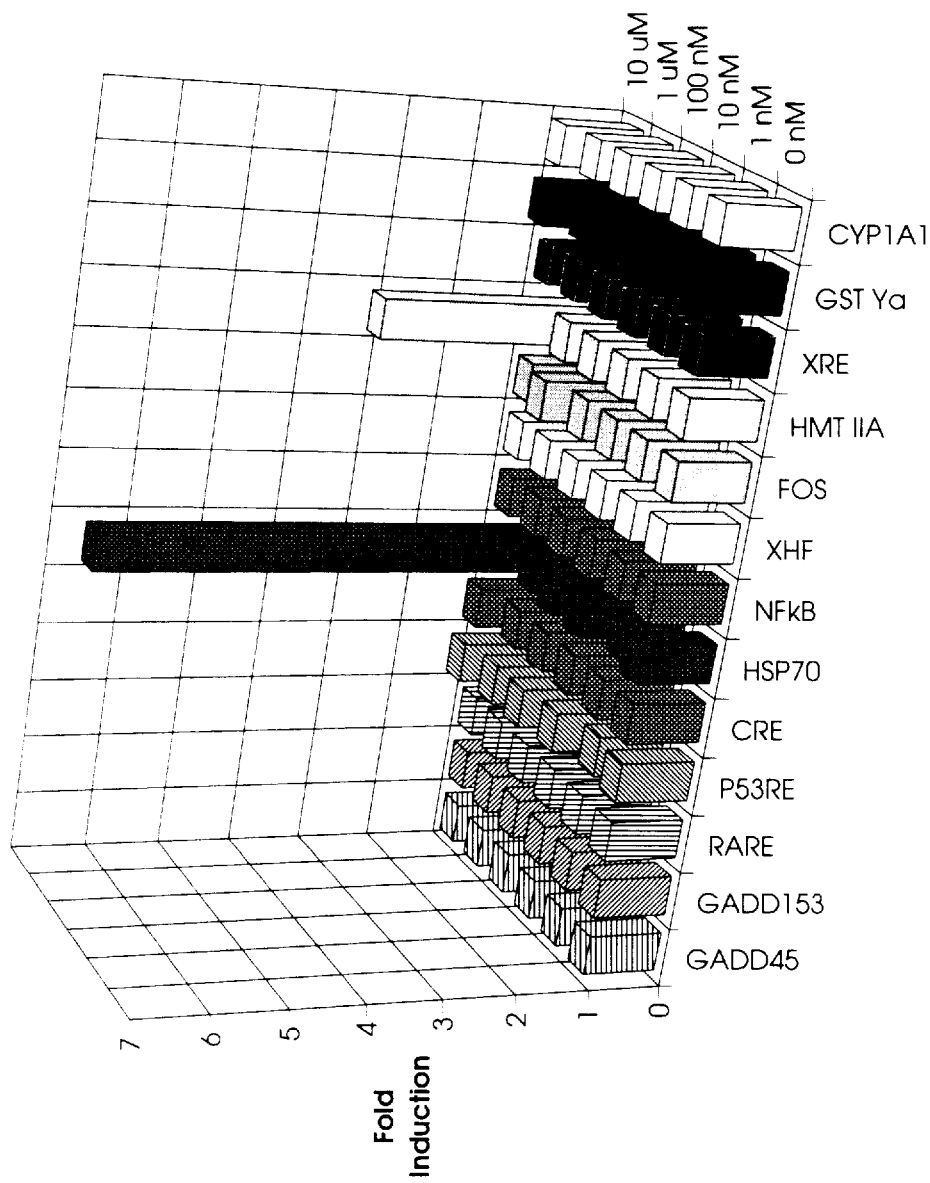
FIG. 9 depicts the relative expression of chloramphenicol acetyl transferase under the control of different stress promoters in the presence of varying concentrations of sodium arsenate.
Figure 10:
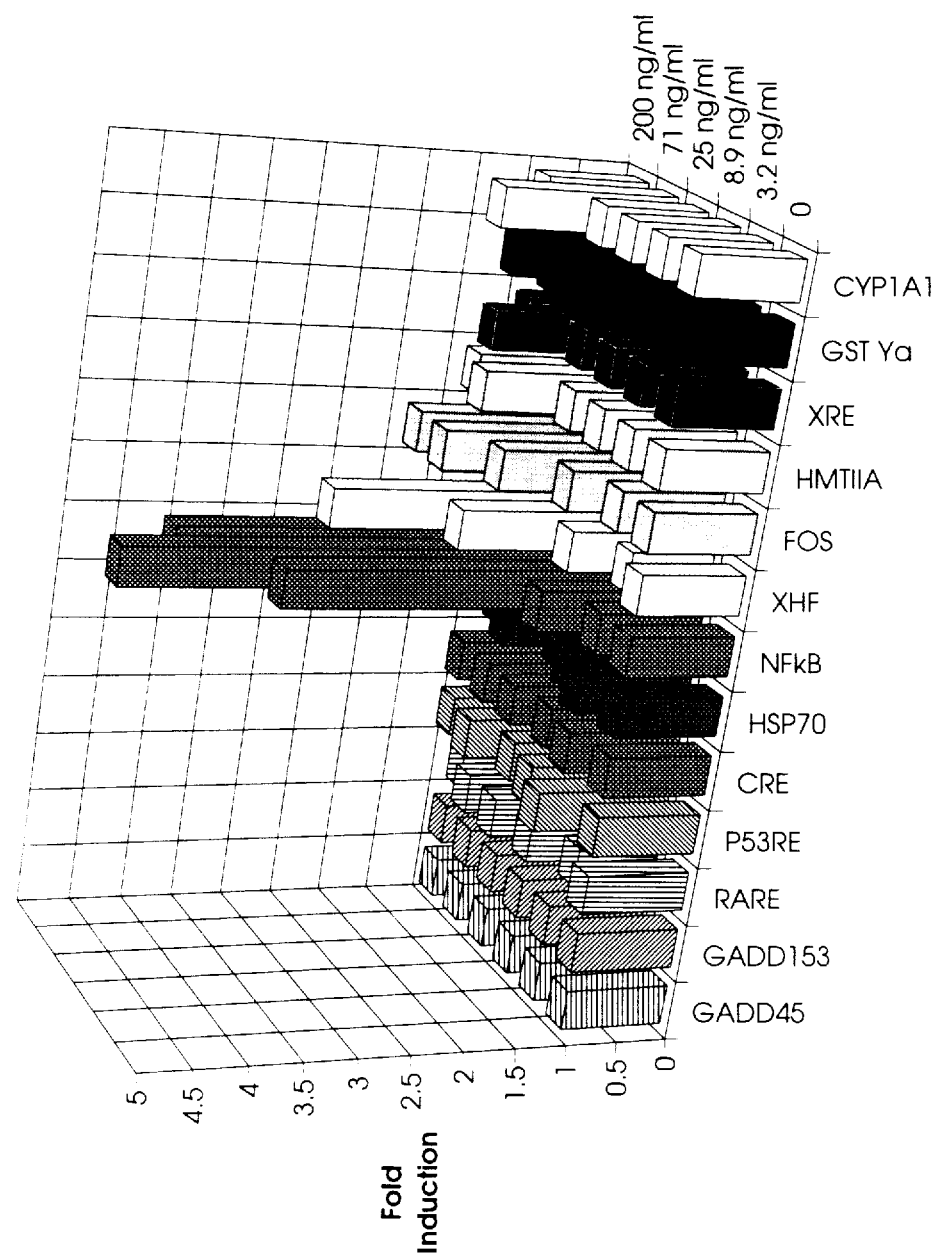
FIG. 10 depicts the relative expression of chloramphenicol acetyl transferase under the control of different stress promoters in the presence of varying concentrations of phorbol 12-acetate-13-myristate (PMA).
Figure 11:
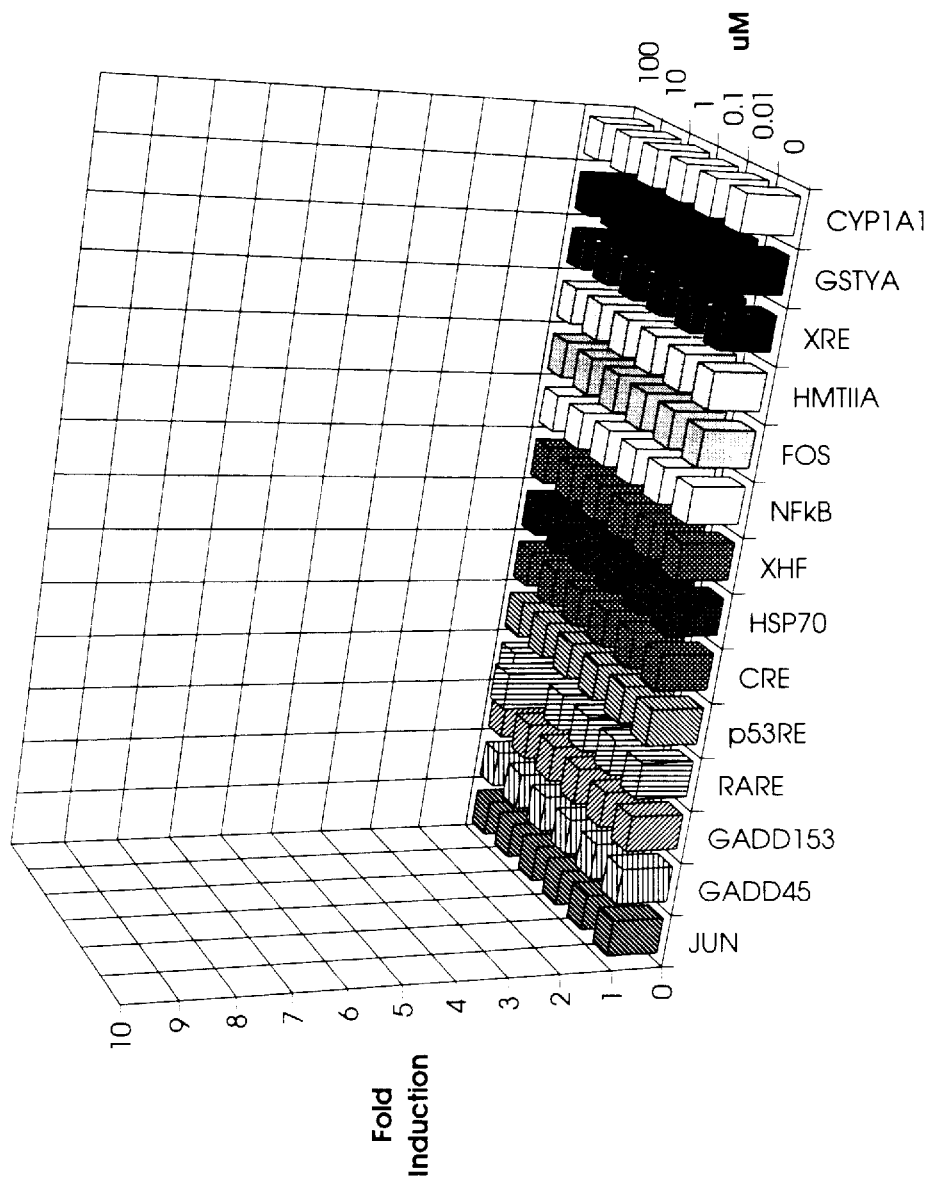
FIG. 11 depicts the relative expression of chloramphenicol acetyl transferase under the control of different stress promoters in the presence of varying concentrations of retinoic acid.

The results for each of these experiments is shown graphically in FIGS. 1–11.

EXAMPLE 6

Identification of Antitoxins

After an unknown compound is found to be a toxin on the basis of its induction of one or more mammalian stress promoters, the same process can be utilized to identify a potential antitoxin.

An unknown compound is demonstrated to induce the HMO promoter and the GADD1S3 promoter in any of the assays described herein. This indicates that the compound is causing oxidative stress and DNA damage. One possibility is that the compound is causing hydrogen peroxide formation in sufficiently high amounts to result in DNA strand breaks. Ascorbic acid is known to reduce the number of hydrogen peroxide-induced DNA strand breaks, and therefore is a potential antitoxin to this unknown compound.

HepG2 cells are grown as described in Example 2. The cells are then incubated with varying dilutions of ascorbic acid for 30 minutes. The cells are then exposed to the concentration of unknown compound previously determined to be optimum for inducing the HMO and GADD153 promoters. The assay for promoter induction (and concomitant stress gene expression) is then carried out as described in Example 2. If the ascorbic acid-treated cells produce a lower level of HMO or GADD1S3 mRNA transcripts than control cells, it is considered to be an antitoxin.

While I have hereinbefore presented a number of embodiments of this invention, it is apparent that my basic construction can be altered to provide other embodiments which utilize the diagnostic kits, processes and products of this invention. Therefore, it will be appreciated that the scope of this invention is to be defined by the claims appended hereto rather than the specific embodiments which have been presented hereinbefore by way of example.

---

We claim:

1. A diagnostic kit for identifying disturbances of the biochemical and biophysical homeostasis of a cell caused by a compound comprising:
   (a) an eukaryotic cell comprising:
      (i) at least one promoter or response element which responds to disturbances of the homeostatic redox state in the cell, wherein said disturbances include conditions which vary the normal reduction or oxidation potential state of a cell and conditions which cause proliferation of peroxisomes;
      (ii) at least one promoter or response element which responds to disturbances of the homeostatic state of DNA in the cell, wherein said disturbances include alterations of deoxyribonucleic acids, alterations of precursor nucleotides, inhibition of DNA synthesis, inhibition of DNA replication, inhibition of mitosis or meiosis;
      (iii) at least one promoter or response element which responds to disturbances of the homeostatic state of proteins in the cell, wherein said disturbances include alterations of proteins or individual amino acids, inhibition of enzyme functions, and perturbations of intracellular transport of proteins; and
      (iv) at least one promoter or response element which responds to disturbances of the homeostatic energy and/or ionic state of the cell, wherein said disturbances include conditions which affect ATP levels, or ionic gradients across a cell membrane,
   each of said promoters or response elements being operatively linked to a separate gene which encodes a detectable product;
   (b) at least four different nucleic acid sequences, each of said nucleic acid sequences being capable of hybridizing under conditions of high stringency to an mRNA transcript of a different one of the genes that is operatively linked to said promoters or response elements or to a single stranded cDNA prepared from said mRNA transcript; and
   (c) means for quantifying the nucleic acid sequences that hybridize to each of said mRNA transcripts or to single stranded cDNA prepared from each of said mRNA transcripts.

2. A method for identifying disturbances of the biochemical and biophysical homeostasis of a cell caused by a compound comprising the steps of:
   (a) exposing to said compound:
      (i) a eukaryotic cell comprising at least one promoter or response element which responds to disturbances of the homeostatic redox state in the cell, wherein said disturbances include conditions which vary the normal reduction or oxidation potential state of a cell and conditions which cause proliferation of peroxisomes;
      (ii) a eukaryotic cell comprising at least one promoter or response element which responds to disturbances of the homeostatic state of DNA in the cell, wherein said disturbances include alterations of deoxyribonucleic acids, alterations of precursor nucleotides, inhibition of DNA synthesis, inhibition of DNA replication, inhibition of mitosis or meiosis;
      (iii) a eukaryotic cell comprising at least one promoter or response element which responds to disturbances to the homeostatic state of proteins in the cell, including alterations to proteins or individual amino acids, inhibition of enzyme functions, and perturbations of intracellular transport of proteins; and
      (iv) a eukaryotic cell comprising at least one promoter or response element which responds to disturbances to the homeostatic energy or ionic state of the cell, including conditions which affect ATP levels, or ionic gradients across a cell membrane;
   wherein each of said promoters or response elements is operatively linked to a gene, either the same or different, encoding a detectable product;
   (b) quantifying the product of each of said genes; and
   (c) creating a promoter induction profile for said compound.

3. The diagnostic kit according to claim 1, wherein said eukaryotic cell is a mammalian cell which additionally comprises:
   a promoter or response element which responds to conditions which alter the transcription level of genes whose expression is regulated by the interaction of a cell surface receptor with a ligand, said promoter or response element being operatively linked to a gene which encodes a detectable product, and
   wherein said kit further comprises at least one nucleic acid sequence which is capable of hybridizing to either an mRNA transcript of said gene which is operatively linked to said promoter or response element which responds to conditions which alter the transcription levels of genes whose expression is regulated by the interaction of a cell surface receptor with a ligand or a single stranded cDNA reverse transcribed from the mRNA transcript of.

4. A diagnostic kit for identifying disturbances of the biochemical and biophysical homeostasis of a cell caused by a compound comprising:

(a) an eukaryotic cell which comprises at least one promoter or response element that responds to disturbances of the homeostatic redox state in the cell, including conditions which vary the normal reduction or oxidation potential state of a cell and conditions which cause proliferation of peroxisomes;

(b) an eukaryotic cell which comprises at least one promoter or response element that responds to disturbances of the homeostatic state of DNA in the cell, wherein said disturbances include alterations of deoxyribonucleic acids, alterations of precursor nucleotides, inhibition of DNA synthesis, inhibition of DNA replication, inhibition of mitosis or meiosis;

(c) an eukaryotic cell which comprises at least one promoter or response element that responds to disturbances of the homeostatic state of proteins in the cell, wherein said disturbances include alterations of proteins or individual amino acids, inhibition of enzyme functions, and perturbations of intracellular transport of proteins; and (d) an eukaryotic cell which harbors at least one promoter or response element that responds to disturbances of the homeostatic energy and/or ionic state of the cell, wherein said disturbances include conditions which affect ATP levels, or ionic gradients across a cell membrane;

wherein, each of said promoters or response elements is operatively linked to a heterologous gene encoding a detectable product; and (e) means for quantifying the amount of said detectable product from each of said eukaryotic cells.

5. The diagnostic kit according to claim 4, additionally comprising a mammalian cell comprising a promoter which responds to conditions which alter the transcription level of genes whose expression is regulated by the interaction of a cell surface receptor with a ligand, said promoter being operatively linked to a heterologous gene encoding a detectable product.

6. The diagnostic kit according to claim 1 or 4, wherein said eukaryotic cell is a mammalian cell.

7. The diagnostic kit according to claim 6, wherein said mammalian cell is a HepG2 cell.

8. The diagnostic kit according to claim 3 or 5, wherein said mammalian cell is a cell derived from the skin or from the eye.

9. The diagnostic kit according to claim 1 or 4, wherein said promoter or response element that responds to disturbances of the homeostatic redox state in the cell is selected from the group consisting of CYP1A1, GST Ya, JUN, XRE, NFkBRE, RARE, ThRE, PPRE, ERE, NMO1, ALDH1, ALDH2, HMO, MnSOD, UGT, CYP11B2, Cu.ZnSOD, ADPRT, GP, FAOxase, PBE, PPAR, EH, CYP2B2, CYP2E1, CYP3A3, P450b, P450d, PPa, PKC, GST2, GAPDH, NQO and ARE promoters or response elements.

10. The diagnostic kit according to claim 1 or 4, wherein said promoter or response element which responds to disturbances of the homeostatic state of DNA in the cell is selected from the group consisting of GST Ya, GADD45, JUN, FOS, XHF, GADD153, TRE, p53RE, HMO, DRA, MnSOD, MDR-1, EGR-1, GAS 2,3, MGMT, DNA Pol, beta-pol, DHFR, TK, PCNA, PGHS, LOX, ISG15, 2'-5' AS, EH, CYP2E1, TPO1, TPO2, PCNA and PPa promoters or response elements.

11. The diagnostic kit according to claim 1 or 4, wherein said promoter or response element which responds to disturbances of the homeostatic state of proteins in the cell is selected from the group consisting of GRP78, JUN, FOS, HSP70, MT 1A, MT IIA, MT III and GP promoters or response elements.

12. The diagnostic kit according to claim 1 or 4, wherein said promoter or response element which responds to disturbances to the homeostatic energy and/or ionic state of the cell is selected from the group consisting of GRP78, FOS, CRE, CYP11B2, 2'-5' AS, TH, DBH, ODC, CYP2E1, G6PD, PKC and PVALB promoters or response elements.

13. The diagnostic kit according to claim 3 or 5, wherein said promoter or response element which responds to conditions which alter the transcription level of genes whose expression is regulated by the interaction of a cell surface receptor with a ligand is selected from the group consisting of IL-1 alpha, G-CSF, GM-CSF, TNF alpha, IL-3, IL-8, IL-6, ICAM-1, IL-10 and M-CSF promoters or response elements.

14. The diagnostic kit according to claim 1, wherein said promoters or response elements are selected from the group consisting of ALDH1, CYP1A1, FOS, GADD153, HMO, HSP70, JUN and MTIIA promoters or response elements; and said eukaryotic cell is a HepG2 cell.

15. The diagnostic kit according to claim 4, wherein said promoters or response elements are selected from the group consisting of CYP1A1, GST Ya, GADD45, FOS, XHF, HSP70, MT IIA, GADD153, CRE, XRE, NFkBRE, RARE and p53RE promoters or response elements; and said eukaryotic cells are HepG2 cells.

16. The diagnostic kit according to claim 15, wherein said gene encoding a detectable product is the CAT gene.

17. A method for identifying the disturbances of the biochemical and biophysical homeostasis of a cell caused by a compound comprising the steps of:

(a) culturing:

(i) a eukaryotic cell comprising at least one promoter or response element which responds to disturbances of the homeostatic redox state in the cell, wherein said disturbances include conditions which vary the normal reduction or oxidation potential state of a cell and conditions which cause proliferation of peroxisomes;

(ii) a eukaryotic cell comprising at least one promoter or response element which responds to disturbances to the homeostatic state of DNA in the cell, wherein said disturbances include alterations of deoxyribonucleic acids, alterations of precursor nucleotides, inhibition of DNA synthesis, inhibition of DNA replication, inhibition of mitosis or meiosis;

(iii) a eukaryotic cell comprising at least one promoter or response element which responds to disturbances of the homeostatic state of proteins in the cell, including alterations of proteins or individual amino acids, inhibition of enzyme functions, and perturbations of intracellular transport of proteins; and (iv) a eukaryotic cell comprising at least one promoter or response element which responds to disturbances to the homeostatic energy or ionic state of the cell, including conditions which affect ATP levels, or ionic gradients across a cell membrane;

wherein each of said promoters or response elements is operatively linked to a gene, either the same or different, encoding a detectable product;

(b) exposing said cells to said compound;

(c) quantifying the product of each of said genes; and (d) creating a promoter induction profile for said compound.

18. The method according to claim 1 or claim 2, wherein said eukaryotic cell is a mammalian cell which further comprises at least one promoter or response element which responds to conditions which alter the transcription level of genes whose expression is regulated by the interaction of a cell surface receptor with a ligand.

19. The method according to any one of claims 2, 17 or 18, wherein:

(a) each of said promoters or response elements is operatively linked to the same gene encoding a detectable product, said gene being heterologous to each of said promoters or response elements; and (b) each of said cells comprises a different promoter or response element operatively linked to said gene and is cultured separately prior to exposure to said compound.

20. The method according to claim 2 or claim 17, wherein said eukaryotic cell is a mammalian cell.

21. The method according to claim 18, wherein said mammalian cell is derived from the skin or the eye.

22. The method according to claim 19, wherein said cell is a mammalian cell.

23. The method according to claim 20, wherein said mammalian cell is HepG2.

24. The method according to any one of claims 2, 17 or 18, wherein said promoter or response element that responds to disturbances of the homeostatic redox state in the cell is selected from the group consisting of CYP1A1, GST Ya, JUN, XRE, NFkBRE, RARE, ThRE, PPRE, ERE, NMO1, ALDH1, ALDH2, HMO, MnSOD, UGT, CYP11B2, Cu.ZnSOD, ADPRT, GP, FAOxase, PBE, PPAR, EH, CYP2B2, CYP2E1, CYP3A3, P450b, P450d, PPa, PKC, GST2, GAPDH, NQO and ARE promoters or response elements.

25. The method according to any one of claims 2, 17 or 18, wherein said promoter or response element that responds to disturbances of the homeostatic state of DNA in the cell is selected from the group consisting of GST Ya, GADD45, JUN, FOS, XHF, GADD153, TRE, p53RE, HMO, DRA, MnSOD, MDR-1, EGR-1, GAS 2,3, MGMT, DNA Pol, beta-pol, DHFR, TK, PCNA, PGHS, LOX, ISG15, 2'-5' AS, EH, CYP2E1, TPO1, TPO2, PCNA and PPa promoters or response elements.

26. The method according to any one of claims 2, 17 or 18, wherein said promoter or response element that responds to disturbances of the homeostatic state of proteins in the cell is selected from the group consisting of GRP78, JUN, FOS, HSP70, MT 1A, MT IIA, MT III and GP promoters or response elements.

27. The method according to any one of claims 2, 17 or 18, wherein said promoter or response element that responds to disturbances of the homeostatic energy or ionic state of the cell is selected from the group consisting of GRP78, FOS, CRE, CYP11B2, 2'-5' AS, TH, DBH, ODC, CYP2E1, G6PD, PKC and PVALB promoters or response elements.

28. The method according to claim 18, wherein said promoter or response element that responds to conditions which alter the transcription level of genes whose expression is regulated by the interaction of a cell surface receptor with a ligand is selected from the group consisting of IL-1 alpha, G-CSF, GM-CSF, TNF alpha, IL-3, IL-8, IL-6, ICAM-1, IL-10 and M-CSF promoters or response elements.

29. The method according to claim 2 or claim 17, wherein the quantitation of the gene products comprises the steps of:

(a) isolating mRNA from said culture;

(b) quantitating the amount of mRNA transcribed from each of said genes that is operatively linked to a promoter or response element.

30. The method according to claim 2 or claim 17, wherein said gene encoding a detectable product is the CAT gene.

31. The method according to any one of claims 2, 17 or 18, comprising the additional step of incubating said compound with an S9 liver extract prior to exposing said cells to said compound.

32. The method according to claim 30, wherein said promoters or response elements are selected from the group consisting of CYP1A1, GST Ya, GADD45, FOS, XHF, HSP70, MT IIA, GADD153, CRE, XRE, NFkBRE, RARE and p53RE promoters or response elements; and said mammalian cells are HepG2 cells.

33. A method of determining if an agent, which decreases disturbances of the biochemical and biophysical homeostasis of a cell caused by a first compound, can also decrease disturbances of the biochemical and biophysical homeostasis of a cell caused by a second compound comprising the steps of:

(a) identifying the disturbances caused by said second compound by the method according to claim 17 or claim 2, thereby generating a promoter induction profile for the second compound;

(b) identifying a first compound which, in the method according to any one of claims 17–32 or claim 2, causes disturbances of the biochemical and biophysical homeostasis of a cell similar to those caused by said second compound;

(c) identifying an agent that decreases the homeostatic disturbances caused by said first compound;

(d) repeating step (a) in the presence of the agent identified in step (c); and (e) comparing the induction profile created in step (a) with the induction profile created in step (d) to determine if said agent reduced the disturbances of the biochemical and biophysical homeostasis of a cell caused by said second compound.

34. A method of determining whether disturbances of the biochemical and biophysical homeostasis of a cell caused by a drug can be reduced by modifying said drug, comprising the steps of:

(a) identifying the disturbances of the biochemical and biophysical homeostasis of a cell caused by said drug using the methods according to claim 2 or claim 17;

(b) modifying said drug to alter or eliminate the portion thereof suspected of causing said identified homeostatic disturbances;

(c) identifying the disturbances of the biochemical and biophysical homeostasis of a cell caused by said modified drug using the methods according to claim 2 or claim 17; and (d) comprising the induction profile of said drug with a promoter induction profile of said modified drug to determine whether said modification reduced the homeostatic disturbances caused by said drug wherein a decrease in the induction of the promoter or response element indicates the reduction of homeostatic disturbances caused by said drug.

35. The method according to claim 2 or claim 17, wherein each of said promoters or response elements is operatively linked to the same gene.

36. The method according to claim 2 or claim 17, wherein each of said promoters or response elements is operatively linked to a separate gene.

37. The method according to claim 2 wherein said alterations of deoxyribonucleic acids are caused by exposure to growth factors, interferons, tumor promoters, tumor necrosis factor, phorbol esters, hydrophobic cytotoxic drugs, inflammatory agents, mitogens, carcinogens, X-rays, UV radiation or dimethylnitrosamines.

38. The kit according to claim 1 wherein said alterations of deoxyribonucleic acids are caused by exposure to growth factors, interferons, tumor promoters, tumor necrosis factor, phorbol esters, hydrophobic cytotoxic drugs, inflammatory agents, mitogens, carcinogens, X-rays, UV radiation or dimethylnitrosamines.

39. The kit according to claim 4 wherein said alterations of deoxyribonucleic acids are caused by exposure to growth factors, interferons, tumor promoters, tumor necrosis factor, phorbol esters, hydrophobic cytotoxic drugs, inflammatory agents, mitogens, carcinogens, X-rays, UV radiation or dimethylnitrosamines.

40. The kit according to claim 17 wherein said alterations of deoxyribonucleic acids are caused by exposure to growth factors, interferons, tumor promoters, tumor necrosis factor, phorbol esters, hydrophobic cytotoxic drugs, inflammatory agents, mitogens, carcinogens, X-rays, UV radiation or dimethylnitrosamines.

* * * * *